United States Patent [19]
Greenlee et al.

[11] Patent Number: 5,187,159
[45] Date of Patent: Feb. 16, 1993

[54] ANGIOTENSIN II ANTAGONISTS INCORPORATING A SUBSTITUTED 1,3-BENZODIOXOLE OR 1,3-BENZODITHIOLE

[75] Inventors: William J. Greenlee, Teaneck; Ralph A. Rivero, Eatontown, both of N.J.

[73] Assignee: Merck & Co., Inc., Rahway, N.J.

[21] Appl. No.: 773,070

[22] Filed: Oct. 7, 1991

[51] Int. Cl.$^5$ .................. A61K 31/435; C07D 471/04
[52] U.S. Cl. .................. 514/81; 514/234.2; 514/303; 544/127; 546/23; 546/118; 548/305.1; 548/305.7; 548/111; 548/113
[58] Field of Search .................. 546/23, 118; 544/127; 514/81, 234.2, 303

[56] References Cited
FOREIGN PATENT DOCUMENTS

| | | |
|---|---|---|
| 253310 | 7/1987 | European Pat. Off. |
| 399731 | 5/1990 | European Pat. Off. |
| 399732 | 5/1990 | European Pat. Off. |
| 400974 | 5/1990 | European Pat. Off. |
| 429257 | 11/1990 | European Pat. Off. |
| 430709 | 11/1990 | European Pat. Off. |
| 434249 | 11/1990 | European Pat. Off. |

WO91/11999 2/1991 PCT Int'l Appl.

*Primary Examiner*—Bernard Dentz
*Attorney, Agent, or Firm*—Valerie J. Camara; William H. Nicholson; Joseph F. DiPrima

[57] ABSTRACT

1,3-Benzodioxoles and 1,3-benzodithioles substituted with a 6-fused imidazole of Formula I which are useful as angiotensin II antagonists.

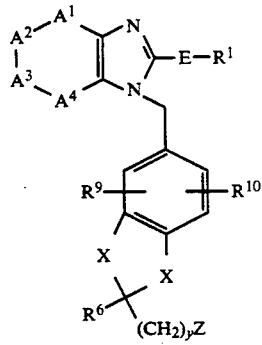

9 Claims, No Drawings

/ 1

ANGIOTENSIN II ANTAGONISTS INCORPORATING A SUBSTITUTED 1,3-BENZODIOXOLE OR 1,3-BENZODITHIOLE

BACKGROUND OF THE INVENTION

The Renin-angiotensin system (RAS) plays a central role in the regulation of normal blood pressure and seems to be critically involved in hypertension development and maintenance as well as congestive heart failure. Angiotensin II (A II), is an octapeptide hormone produced mainly in the blood during the cleavage of angiotensin I by angiotensin converting enzyme (ACE) localized on the endothelium of blood vessels of lung, kidney, and many other organs. It is the end product of the renin angiotensin system (RAS) and is a powerful arterial vasoconstrictor that exerts its action by interacting with specific receptors present on cell membranes. One of the possible modes of controlling the RAS is angiotensin II receptor antagonism. Several peptide analogs of A II are known to inhibit the effect of this hormone by competitively blocking the receptors, but their experimental and clinical applications have been limited by partial agonist activity and lack of oral absorption [M. Antonaccio. Clin. Exp. Hypertens. A4, 27–46 (1982); D. H. P. Streeten and G. H. Anderson, Jr.—Handbook of Hypertension, Clinical Pharmacology of Antihypertensive Drugs, ed. A. E. Doyle, Vol. 5, pp. 246–271, Elsevier Science Publisher, Amsterdam, The Netherlands, 1984].

Recently, several non-peptide compounds have been described as A II antagonists. Illustrative of such compounds are those discussed in U.S. Pat. Nos. 4,207,324; 4,340,598; 4,576,958; and 4,582,847 in European Patent Applications 028,834; 245,637; 253,310; and 291,969; and in articles by A. T. Chiu, et al. [Eur. J. Pharm. Exp. Therap., 157, 13–21 (1988)] and by P. C. Wong, et al. [J. Pharm. Exp. Therap., 247, 1–7(1988)]. All of the U.S. Patents, European Patent Applications 028,834 and 253,310 and the two articles disclose substituted imidazole compounds which are generally bonded through a lower alkyl bridge to a substituted phenyl. European Patent Application 245,637 discloses derivatives of 4,5,6,7-tetrahydro-2H-imidazo[4,5-c]-pyridine-6-carboxylic acid and analogs thereof as antihypertensive agents.

None of the compounds disclosed in this application have been identified in any U.S. Patent, European Applications or articles. The substituted imidazoles, have been disclosed in patents to DuPont (EPO 253,310 and EPO 324,377) focusing on the design of Angiotensin II Antagonists. Substituted benzimidazole containing compounds useful as angiotensin II antagonists have been disclosed in U.S. Pat. No. 4,880,804 and European Patent Application 392,317. Substituted imidazopyridine containing compounds useful as angiotensin II antagonists have also been disclosed in European Patent Applications 260,613, 399,731 and 412,848 and U.S. Ser. No. 516,286 (filed May 4, 1990).

BRIEF DESCRIPTION OF THE INVENTION

The compounds of Formula (I) are angiotensin II antagonists and are useful in the treatment of hypertension and congestive heart failure. Additionally, pharmaceutically acceptable compositions of these novel compounds, as the sole therapeutically active ingredient and in combination with diuretics and other antihypertensive agents, including beta-blockers, angiotensin converting enzyme inhibitors, calcium channel blockers or a combination thereof are disclosed. Further, methods of treating hypertension, congestive heart failure and elevated intraocular pressure are described and claimed.

The compounds of this invention have central nervous system (CNS) activity. They are useful in the treatment of cognitive dysfunctions including Alzheimer's disease, amnesia and senile dementia. These compounds also have anxiolytic and antidepressant properties and are therefore, useful in the relief of symptoms of anxiety and tension and in the treatment of patients with depressed or dysphoric mental states.

DETAILED DESCRIPTION OF THE INVENTION

The compounds of the invention herein described having a structural formula:

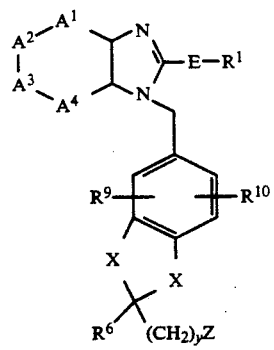

or a pharmaceutically acceptable salt thereof wherein:
$R^1$ is:
(a) $(C_1-C_6)$-alkyl, $(C_2-C_6)$-alkenyl or $(C_2-C_6)$-alkynyl each of which can be unsubstituted or substituted with a substituent selected from the group consisting of:
  i) aryl as defined below in $R^1(b)$,
  ii) $(C_3-C_7)$-cycloalkyl,
  iii) Cl, Br, I, F,
  (iv) OH,
  v) $NH_2$,
  vi) $NH(C_1-C_4)$-alkyl,
  vii) $N[((C_1-C_4)$-alkyl$)]_2$,
  viii) $NHSO_2R^2$,
  ix) $CF_3$,
  x) $COOR^2$, or
  xi) $SO_2NHR^{2a}$;
(b) aryl, wherein aryl is defined as phenyl or naphthyl, unsubstituted or substituted with 1 or 2 substituents selected from the group consisting of:
  i) Cl, Br, I, F,
  ii) $(C_1-C_4)$-alkyl,
  iii) $(C_1-C_4)$-alkoxy,
  iv) $NO_2$
  v) $CF_3$
  vi) $SO_2NR^{2a}R^{2a}$,
  vii) $(C_1-C_4)$-alkylthio,
  viii) hydroxy,
  ix) amino,
  x) $(C_3-C_7)$-cycloalkyl,
  xi) $(C_3-C_{10})$-alkenyl; and
(c) heteroaryl, wherein heteroaryl is defined as a 5- or 6-membered heteroaromatic moiety, which can contain one or two members selected from the group consisting of N, O, S and wherein the heteroaryl is optionally mono- or disubstituted with substituents selected from the group consisting of:
  i) Cl, Br, I, F,
  ii) OH,
  iii) SH,
  iv) $NO_2$,
  v) $(C_1-C_4)$-alkyl,
  vi) $(C_2-C_4)$-alkenyl,
  vii) $(C_2-C_4)$-alkynyl,
  viii) $C_1-C_4$-alkoxy, or
  ix) $CF_3$,
(d) $(C_1-C_4)$-perfluoroalkyl,
(e) $(C_3-C_8)$-cycloalkyl, or
(f) $(C_1-C_4)$-alkyl-$(C_3-C_8)$-cycloalkyl;

$-A^1-A^2-A^3-A^4-$ is:
(a) $-C(R^4)=C(R^4)-C(R^4)=C(R^4)-$,
(b) $-C(R^4)=C(R^4)-C(R^4)=N-$,
(c) $-N=C(R^4)-C(R)^4=C(R^4)-$,
(d) $-C(R^4)=N-C(R^4)=C(R^4)-$,
(e) $-C(R^4)=C(R^4)-N=C(R^4)-$,
(f) $-C(R^4)=N-C(R^4)=N-$, or
(g) $-N=C(R^4)-N=C(R^4)-$;

E is:
(a) a single bond,
(b) $-S(O)_n(CH_2)_s-$, or
(c) $-O-$;
n is 0 to 2;
s is 0 to 5;
y is 0 or 1;

X groups are independently;
(a) $-O-$,
(b) $-S(O)_n-$,
(c) $-CH_2-$, or
(d) $-NR^2-$;

$R^2$ is:
(a) H, or
(b) $(C_1-C_6)$-alkyl;

$R^{2a}$ is:
(a) $R^2$,
(b) $CH_2$-aryl, or
(c) aryl;

$R^4$ groups are independently:
(a) H,
(b) $(C_1-C_6)$-alkyl, $(C_2-C_6)$-alkenyl, or $(C_2-C_6)$-alkynyl, each of which is unsubstituted or substituted with a substituent selected from the group consisting of OH, $(C_1-C_4)$-alkoxy, $CO_2R^2$, $OCOR^2$, $CONHR^2$, $CON(R^2)_2$, $N(R^2)C(=O)R^2$, $NH_2$, $NH[(C_1-C_4)$-alkyl], $N[(C_1-C_4)$-alkyl]$_2$,
(c) $-C(=O)$-aryl,
(d) $(C_3-C_7)$-cycloalkyl,
(e) Cl, Br, I, F,
(f) $-OH$,
(g) $-OR^{21}$,
(h) $-CF_3$,
(i) $-SH$,
(j) $-S(O)_n-(C_1-C_4)$-alkyl,
(k) $-CO_2R^{2a}$,
(l) $-SO_3H$,
(m) $-NR^2R^{21}$,
(n) $-NR^2C(O)R^{21}$,
(o) $-NR^2COOR^{21}$,
(q) $-SO_2NR^2R^{2a}$,
(r) $-NO_2$,
(s) $-NHSO_2-(C_1-C_4)$-alkyl,
(t) $-C(O)NHSO_2R^{14}$,
(u) aryl,
(v) heteroaryl, or
(w) morpholin-4-yl;

$R^6$ is:
(a) H,
(b) $(C_1-C_4)$-alkyl,
(c) aryl, wherein aryl is phenyl or naphthyl, substituted or unsubstituted with one or two substituents selected from the group consisting of: $(C_1-C_4)$-alkyl, $(C_1-C_4)$-alkoxyl, $(C_1-C_4)$-alkyl-$S(O)_n-$, $-CO_2R^2$, Cl, Br, I, F, $CONR^2R^{2a}$, $NHCO(C_1-C_4)$-alkyl, $NHCONR^2R^{2a}$, O-phenyl, or S-phenyl; or
(d) aryl-$(C_1-C_2)$-alkyl;

$R^9$ and $R^{10}$ are each independently:
(a) H,
(b) Cl, Br, I, F,
(c) $NO_2$,
(d) $(C_1-C_8)$-alkyl,
(e) $(C_2-C_4)$-alkenyl,
(f) $(C_2-C_4)$-alkynyl,
(g) $(C_1-C_4)$-alkoxy,
(h) $(C_1-C_4)$-alkylthio,
(i) $(C_1-C_4)$-alkylsulfinyl, or
(j) $(C_1-C_4)$-alkylsulfonyl;

Z is:
(a) $-CO_2R^{2a}$,
(b) -tetrazol-5-yl,
(c) $-PO(OH)_2$,
(d) $-CONH(tetrazol-5-yl)$,
(e) $-CH_2CO_2R^{2a}$,
(f) $-CONHSO_2R^{14}$,
when y=0, then Z can be:
(g) $-CO_2R^{2a}$,
(h) -tetrazol-5-yl,
(i) $-CONH(tetrazol)-5-yl)$,
(j) $-NHSO_2CF_3$, or
(k) $-CONHSO_2R^{14}$;

$R^{14}$ is:
(a) aryl, or
(b) heteroaryl,
(c) $(C_3-C_7)$-cycloalkyl, or
(d) $(C_1-C_4)$-alkyl unsubstituted or substituted with a substituent selected from the group consisting of: aryl, heteroaryl, $-OH$, $-SH$, $(C_1-C_4)$-alkyl, $-O(C_1-C_4)$ alkyl, $-S(C_1-C_4)$-alkyl, $-CF_3$, Cl, Br, F, I, $-NO_2$, $-CO_2H$, $CO_2-(C_1-C_4)$-alkyl, $NH_2$, $NH[(C_1C_4)$alkyl], $N[(C_1-C_4)$-alkyl]$_2$, $-PO_3H$, $PO(OH)(O-(C_1-C_4)$-alkyl); and $R^{21}$ is:
(a) H, or
(b) $(C_1-C_4)$-alkyl, unsubstituted or substituted with a substituent selected from the group consisting of: $NH_2$, $NH[(C_1-C_4)$-alkyl], $N[(C_1-C_4)$-alkyl]$_2$, $CO_2H$, $CO_2(C_1-C_4)$-alkyl, OH, $SO_3H$, or $SO_2NH_2$.

The alkyl substituents recited above denote straight and branched chain hydrocarbons of the length specified such as methyl, ethyl, isopropyl, isobutyl, neopentyl, isopentyl, etc.

The alkenyl an alkynyl substituents denote alkyl groups as described above which are modified so that each contains a carbon to carbon double bond or triple bond, respectively, such as vinyl, allyl and 2-butenyl.

Cycloalkyl denotes rings composed of 3 to 8 methylene groups, each which may be substituted or unsubstituted with other hydrocarbon substituents, and include for example cyclopropyl, cyclopentyl, cyclohexyl and 4-methylcyclohexaneyl.

The alkoxy substituent represents an alkyl group as described above attached through an oxygen bridge.

The aryl substituent recited above represents phenyl or naphthyl.

The heteroaryl substituent recited above represents any 5- or 6-membered aromatic ring containing from one to three heteroatoms selected from the group consisting of nitrogen, oxygen, and sulfur, for example, pyridyl, thienyl, furyl, imidazolyl, and thiazolyl.

GENERAL METHODS FOR PREPARATIONS OF COMPOUNDS OF GENERAL FORMULA I

The methods described in PART I and PART II below illustrate the preparation of angiotensin II antagonists of Formula I. There are several general approaches to the synthesis of antagonists of Formula I, and it is taken as a general principle that one or another method may be more readily applicable for the preparation of a given antagonist; some of the approaches illustrated below may not be readily applicable for the preparation of certain antagonists of Formula I.

It should be recognized that antagonists of Formula I consist of a heterocyclic component designated above by formula I and a 1,3-benzodioxide or 1,3-benzodithiole derivative which is attached to the heterocyclic component through a nitrogen atom. Thus, two generally applicable approaches to antagonists of formula I are these:

A heterocycle, designated above as a fused imidazole in Formula I is prepared as described in PART I below. Then the heterocycle is alkylated at a nitrogen atom with a halomethyl 1,3-benzodioxole or 1,3-benzodithiole derivative giving the compounds of Formula I. The preparation of the halomethyl 1,3-benzodioxole or 1,3-benzodithiole derivatives are described in Part II below. This alkylating agent is often designated as "Ar—CH2Q where Q is a halide (—Cl,Br,I) or pseudohalide (—OMs, OTs, OTf). In some cases, alkylation may take place at more than one nitrogen atom of the heterocycle, and in these cases, separation by fractional crystallization or by chromotographic methods may be necessary for isolation of the desired product. In some cases, the alkylation step produces a fully-assembled antagonist of Formula I, except that functional groups on the alkylating agent or on the heterocycle may be present in protected form and require deprotection steps to be carried out to complete the synthesis. In some cases, the alkylation is carried out with only a partially assembled benzodioxide or benzodithiole (substituted halomethyl catechol derivatives) and requires subsequent steps to give the antagonist of Formula I. The alkylation steps and subsequent steps used to prepare antagonists of Formula I, are described in PART II below.

The compounds of this invention maybe resolved using techniques known in the art. The diastereomeric salts or esters of the enantiomers are separated and the desired compound is the more active stereoisomer. The compounds of this invention, their pharmaceutically acceptable salts and their prodrug forms are included within the scope of this invention. Abbreviations used in the schemes and examples are listed in Table 1.

TABLE 1

| Reagents | |
|---|---|
| NBS | N-bromosuccinimide |
| AIBN | Azo(bis) isobutyronitrile |
| DDQ | Dichlorodicyanoquinone |

TABLE 1-continued

| | |
|---|---|
| Ac₂O | acetic anhydride |
| TEA | triethylamine |
| DMAP | 4-dimethylaminopyridine |
| PPh₃ | triphenylphosphine |
| TFA | trifluroacetic acid |
| TMS-Cl | trimethylsilyl chloride |
| Im | imidazole |
| AcSK | potassium thioacetate |
| p-TsOH | p-toluenesulfonic acid |
| FMOC-Cl | 9-Fluorenylmethyloxycarbonyl chloride |
| Solvents: | |
| DMF | dimethylformamide |
| HOAc (AcOH) | acetic acid |
| EtOAc (EtAc) | ethyl acetate |
| Hex | hexane |
| THF | tetrahydrofuran |
| DMSO | dimethylsulfoxide |
| MeOH | methanol |
| iPrOH | isopropanol |
| Others: | |
| r t | room temperature |
| TBDMS | t-butyldimethylsilyl |
| OTf | OSO₂CF₃ |
| Ph | phenyl |
| FAB-MS (FSBMS) | Fast atom bombardment mass spectroscopy |
| NOE | Nuclear Overhauser Effect |
| SiO₂ | silica gel |
| trityl | triphenylmethyl |

PART I

Preparation of the 6-Fused Imidazole Heterocycles

BENZIMIDAZOLES

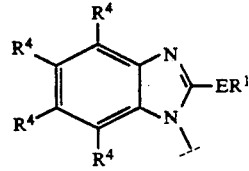

The compounds of Formula I wherein (—A¹—A²—A³—A⁴—) is a 4-atoms sequence as defined in the General Description of the invention can be synthesized using the reactions and techniques described herein below. The reactions are performed in a solvent appropriate to the reagents and materials employed and suitable for the transformation being effected. It is understood by those skilled in the art of organic synthesis that the functionality present on the benzimidazole and other parts of the structure should be consistent with the chemical transformations proposed. Depending upon the reactions and techniques employed, this may involve changing the order of synthetic steps, use of required protecting groups followed by deprotection, and activation of the benzylic position of the alkylating agents used to enable alkylation at the nitrogen on the imidazole part of benzimidazoles.

The synthetic routes for preparing benzimidazole containing antagonists are disclosed in European Patent application, EP 400835, published on Dec. 5, 1990.

SCHEME I-1

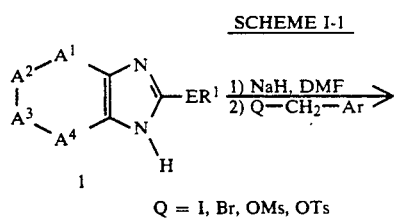

Q = I, Br, OMs, OTs

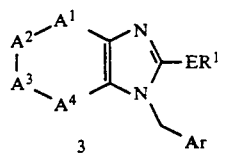

REACTION SCHEME I-2

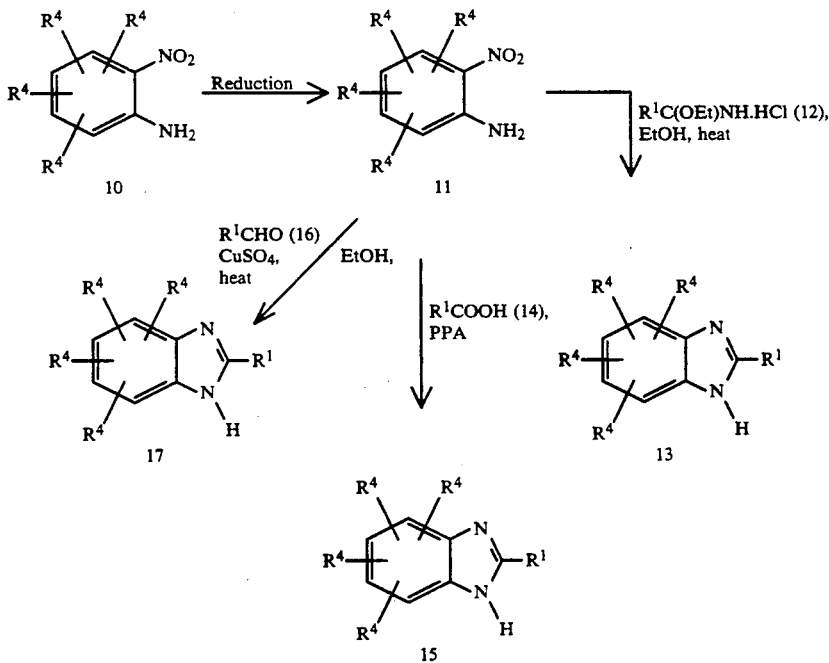

As shown in Reaction Scheme I-1, compounds of Formula (3) can be prepared by carrying out direct alkylation of alkali-metal salt of benzimidazole (1) (preparation of benzimidazoles are described in Schemes I-2 to I-5) using appropriately protected benzyl halide, tosylate (OTs) or mesylate (OMs) derivatives (2). The salt is prepared preferably using MH (where M is lithium, sodium or potassium) in anhydrous dimethylformamide (DMF), or by treating it with metal alkoxide such as sodium or potassium methoxide, ethoxide or t-butoxide in an appropriate alcohol such as methanol, ethanol or t-butanol as the solvent. The alkylation is generally carried-out by dissolving the metal salt of benzimidazole in a dipolar aprotic solvent such as DMF or dimethylsulfoxide (DMSO) and reacting it with the alkylating agent at 20° C. to reflux temperature of the solvent for 1-24 hours.

If substituents on the benzene ring result in an unsymmetrical benzimidazole, the alkylation may produce a mixture of two regioisomers as products. These regioisomers possess distinct physico-chemical and biological properties and in most cases can be separated and purified by using conventional separation techniques such as chromatography (flash column chromatography, medium-pressure liquid chromatography, high pressure liquid chromatography (HPLC) and/or crystallization. In those cases where separation of regioisomers is difficult by conventional techniques, the mixture can be transformed into suitable derivatives that can be separated by usual separation methods. The structural assignments of the isomers can be made using proton NMR, Nuclear Overhauser Effect (NOE) experiments or X-ray crystallography.

The starting benzimidazoles can be readily prepared by any of the standard procedures described in the literature [P. N. Preston, Chemistry of Heterocyclic Compounds, Vol. 40, part I, pp. 1-286 (1981) and references cited therein]. Several alternative routes to obtain benzimidazoles are outlined in Scheme I-2. The most widely used starting material, o-phenylenediamines (11), can be readily prepared from the corresponding o-nitro-aniline (10) using standard reductive procedures such as metal-acid reduction or catalytic reduction. The substituted or unsubstituted (11) can then be treated with an appropriate imidate hydrochloride (12) to form corresponding benzimidazoles (13). Alternatively, the reaction of carboxylic acids (14) with o-phenylenediamines in the presence of polyphosphoric acid (PPA) is also effective in producing benzimidazoles (15). Benzimidazoles (17) can also be prepared from o-phenylenediamines and aldehyde (16) using cupric salt as an oxidant [R. Weidenhagen, Chem. Ber., 69, 2263 (1936)].

SCHEME I-3

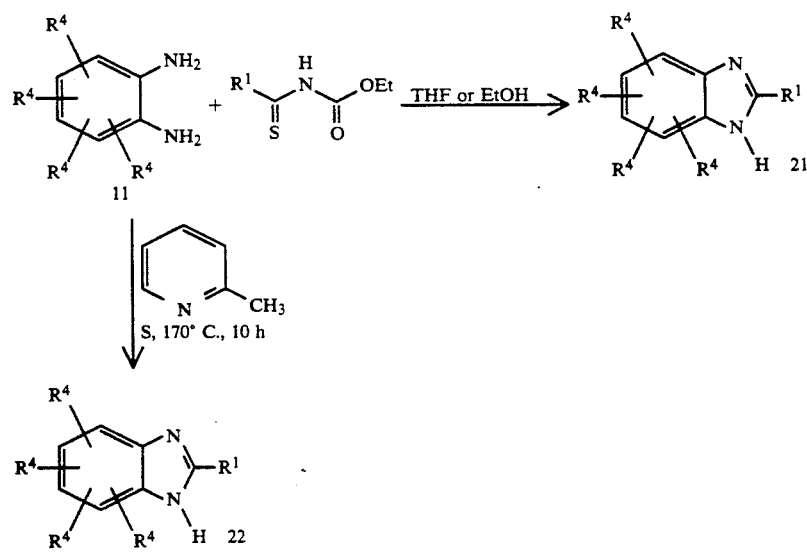

Although some benzimidazoles having aryl and heteroaryl groups at the 2 position can be prepared using the methods described in Reaction Scheme I-2, Scheme I-3 outlines methods which are more suitable for the synthesis of this class of compounds. N'-aryl-N-hydroxyamidines (18; R=OH) are cyclized under mild conditions using benzenesulfonyl chloride in pyridine or triethylamine to give 19 in good yield [M. W. Partridge and H. A. Turner, *J. Chem. Soc.*, 2086 (1958)]. Parent amidines (18; R=H) can also be oxidized with sodium hypochlorite under basic conditions to form 19 [V. J. Grenda, R. E. Jones, G. Gal and M. Sletzinger, *J. Org. Chem.*, 30, 259 (1965)].

Alternatively, as shown in Reaction Scheme I-3, o-phenylenediamines (11) can be reacted with N-ethoxycarbonyl- thioamides (20) to give 2-substituted benzimidazoles (21) in excellent yields. This method avoids the use of acidic catalysts. The reagents (20) are easily obtained in one step from ethoxy- carbonyl isothiocyanate and simple aromatic or heterocyclic compounds or alkylmagnesium halides [B. George and E. P. Papadopoulos., *J. Org. Chem.*, 41, 3233(1976); E. P. Papadopoulos., *J. Org. Chem.*, 41, 962(1976)]. Heterocyclic compounds containing reactive methyl groups (e.g., 2-picoline) can also be reacted with o-phenylenediamines in the presence of sulfur at elevated temperatures to give 2-heteroaryl benzimidazoles (22).

SCHEME I-4

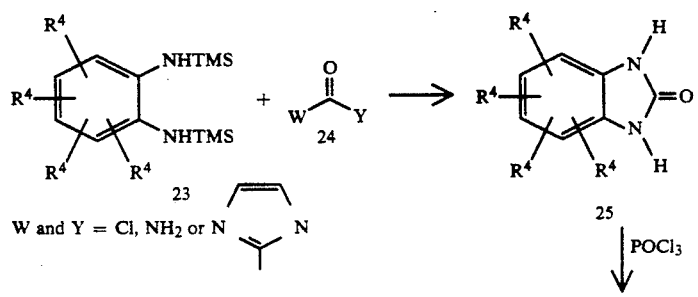

SCHEME I-4

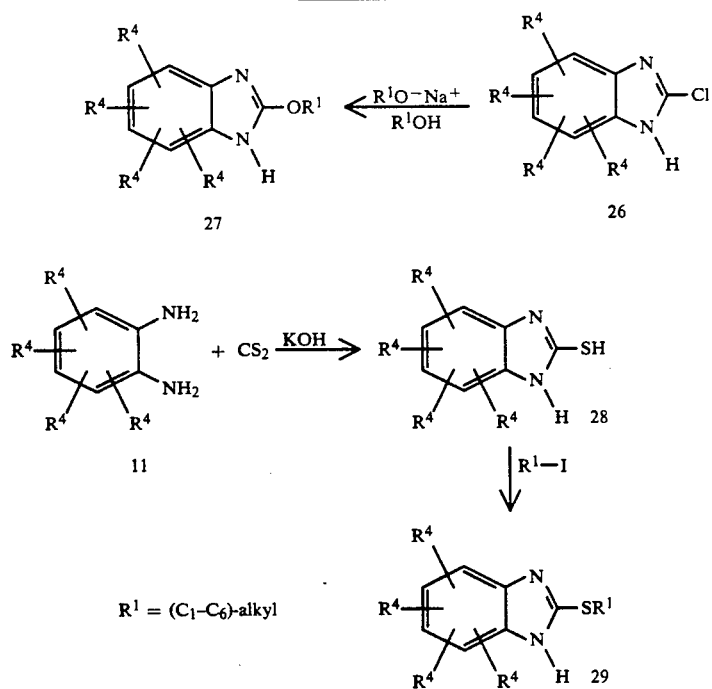

$R^1 = (C_1-C_6)\text{-alkyl}$

As outlined in Reaction Scheme I-4, benzimidazoles containing 2-alkoxy and thioalkyl substituents (27 and 29) can be prepared from the corresponding benzimidazolones (25) or benzimidazolethiones (28). Benzimidazolones are conveniently prepared from o-phenylenediamines and phosgene or urea [K. Hofmann, "Imidazole and its Derivatives, Part 1," Wiley-Interscience, New York, 1953, pp. 285-291]. Carbonate esters, diethylpyrocarbonate, N,N-carbonyldiimidazole and N,N-diethylcarbamyl chloride may also be used in this reaction. The reaction of phosgene is apparently facilitated by the use of N,N'-bis-trimethylsilyl (TMS) derivative (23) instead of parent diamine [L. Birkhofer, H. P. Kuhlthau, and A. Ritter, Chem. Ber., 93, 2810 (1960)].

REACTION SCHEME I-5

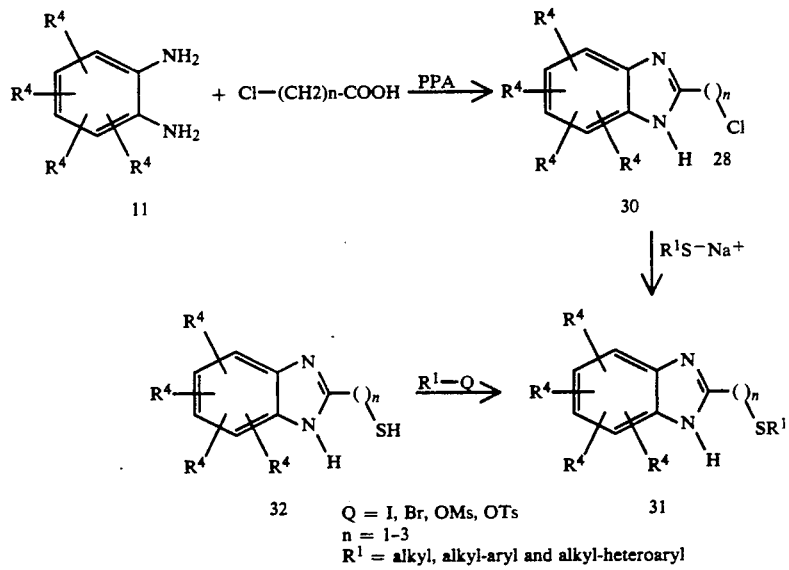

Q = I, Br, OMs, OTs
n = 1-3
$R^1$ = alkyl, alkyl-aryl and alkyl-heteroaryl

As described in Reaction Scheme I-5, 2-alkylthioalkyl substituted benzimidazoles (31) can be prepared from the reaction of RS-M (where M is sodium, potassium or lithium) with 2-chloroalkyl benzimidazoles (30). 2-Chloroalkyl benzimidazoles (30) can be conveniently prepared from the diamines and the chloroalkyl carboxylic acids using PPA [W. Knobloch, Chem. Ber., 91, 2557 (1958)]. Alternatively, compound 31 can also be prepared from the readily available 2-thioalkyl derivative (32) [E. S. Milner, S. Snyder, and M. M. Joullie, J. Chem. Soc., 4151 (1964)].

IMIDAZO-6-FUSED HETEROCYCLES

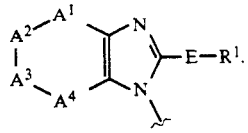

The compounds of Formula I, can be synthesized using the reactions and techniques described herein below. The reactions are performed in a solvent appropriate to the reagents and materials employed and suitable for the transformation being effected. It is understood by those skilled in the art of organic synthesis that the functionality present on the heterocycle and in the reactants being employed should be consistent with the chemical transformations being conducted. Depending upon the reactions and techniques employed, optimal yields may require changing the order of synthetic steps or use of protecting groups followed by deprotection.

The synthetic routes for preparing imidazo-6-fused heterocycles are disclosed in European Patent application, EP 400,974 published on Dec. 5, 1990.

As shown in Reaction Scheme I-1, compounds of Formula I can be prepared by carrying-out direct alkylation of alkali-metal salts of heterocycles (1) using appropriately protected benzyl halide, tosylate (OTs) or mesylate (OMs) derivatives (2). The salt is prepared preferably using MH (where M is lithium, sodium or potassium) in anhydrous dimethylformamide (DMF), or by treating it with a metal alkoxide such as sodium or potassium methoxide, ethoxide or t-butoxide in an appropriate alcohol such as methanol, ethanol or t-butanol as the solvent. The alkylation is generally carried-out by dissolving the metal salt of the heterocycle in a dipolar aprotic solvent such as DMF or dimethylsulfoxide (DMSO) and reacting it with the alkylating agent at 20° C. to reflux temperature of the solvent for 1-24 hours.

If substituents and/or the hetero atom positions in the six membered ring are not symmetrically disposed, the alkylation on the imidazole nitrogen(s) generally produces a mixture of two regioisomers as products arising from $N^1$ and $N^3$ alkylation. These regioisomers I and Ia possess distinct physico-chemical and biological properties and in most cases can be separated and purified by using conventional separation techniques such as chromatography (flash column chromatography, medium-pressure liquid chromatography, high performance liquid chromatography) and/or crystallization. In those cases where separation of regioisomers is difficult by conventional techniques, the mixture can be transformed into suitable derivatives that can be separated by the above separation methods. The structural assignments of the isomers can be made using Nuclear Overhauser Effect (NOE), $^1H$—$^{13}C$ coupled NMR experiments or X-ray crystallography.

When there is potential for alkylation of the 6-membered heterocyclic ring, this can be avoided by the use of suitable protecting groups.

The heterocycles of type (1) can be prepared by any of the standard procedures described in the literature [J. A. Montgomery and J. A. Secrist III in "Comprehensive Heterocyclic Chemistry," Vol. 5, A. R. Katritsky and C. W. Rees Eds., Pergamon Press 1984; pp 567–597 and 631–656 and references cited therein]. As shown in Reaction Scheme I-6, the most widely used starting materials are six member heterocyclic vicinal diamines (9). Fused imidazoles (10) can be prepared by condensation of (9) with an appropriate carboxylic acid, nitrile, imidate ester, or orthoester, either neat, or in a solvent appropriate and compatible with the starting materials and reagents, such as polyphosphoric acid, ethanol, methanol, hydrocarbon solvents, and with a catalytic amount of acid if required. Oxidation of an imine formed by reaction of diamine (9) with an appropriate aldehyde using oxidants such as Cu (II), nitrobenzene, or 2,3-dichloro-5,6-dicyano-1,4-benzoquinone (DDQ) also affords heterocycles (10). Aminoamides (11, W=H) or diamides (11, W=$R^6CO$) can be converted to fused imidazoles (10) by heating neat, or at an elevated temperature in a solvent such as xylene under acidic or neutral conditions.

Halogenation of the imidazo[4,5-b]pyridine ring at the 6-position can be accomplished using $Br_2$, or N-bromosuccinimide. Halogenation of the 7-position can be accomplished by reaction of the corresponding imidazopyridine-4-oxide (prepared by reaction of the imidazopyridine with peracids such as m-chloroperbenzoic acid) with $POCl_3$. When the 7-position is substituted other than hydrogen halogenation at the 5-position of the 4(N)-oxide precursor occurs on treatment with $POCl_3$. Chlorides may be substituted by bromides or iodides by treatment with either HBr or HI, respectively, in a solvent such as acetic acid.

2-Alkyl-imidazo[4,5-b]pyridines can be substituted at the 5, 6, or 7 position by displacement of a halogen at the position by nucleophiles such as cyanide (followed by hydrolysis to obtain carboxylic acids), amines, copper alkoxides, trialkylphosphites, and thiolates. Also, substitution of the halogens, in particular bromides or iodides, can be accomplished by reaction with a coupling partner such as alkylzinc or arylzinc or arylzinc halides, or monoalkylarylphosphonites in the presence of an appropriate metal catalyst such as mickel, palladium, ruthenium, or platinum. In cases where the displacement of a halogen is sluggish or otherwise complicated due to an acidic proton, the imidazopyridine may be benzyl or other arylmethyl groups.

7-Methyl-2-propylimidazo[4,5-b]pyridine-5-carboxylic acid or the 2-ethyl analog is prepared from 7-methyl-2-propylimidazo[4,5-b]pyridiine or the 2-ethyl analog by treatment with m-chloroperoxybenzoic acid to obtain the N-oxide which is then treated with $POCL_3$ to give 5-chloro-7-methyl-2-propylimidazo-[4,5-b]pyridine or 2-ethyl analog. The chloride is then exchanges for a bromide by reaction of 5-chloro-7-methyl-2-propylimidazo[4,5-b]- pyridine or the 2-ethyl analog with HBr in acetic acid. The resulting 5-bromo-7-methyl-2-propylimidazo-[4,5-b]pyridine or 2-ethyl analog is treated with NaH in DMF followed by benzyl bromide to obtain 3-benzyl-5-bromo-7-methyl-2-propylimidazo[4,5-b]pyridine or its corresponding 2-ethyl analog which is in turn treated with CuCN in hot pyridine to obtain 3-benzyl-5-cyano-7-methyl-2-propylimidazo[4,5-b]pyridine or the corresponding 2-ethyl analog. The cyano compound is hydrolyzed to 3-benzyl-7-methyl-2-propylimidazo-[4,5-b]pyridine-5-carboxylic acid or the corresponding 2-ethyl analog by treatment with $H_2SO_4$—$H_2O$. This acid is esterified by reaction with $CH3OH$=$HCl$. The benzyl group is removed by hydrogenation at 1 atm. in MePH—HCl solution using $Pd(OH)_2$ as catalyst. This compound can be alkylated as described earlier and the product methyl ester is converted to the carboxylic acid by treatment with hydroxide.

As shown in Reaction Scheme I-17, methods of preparing heterocycles of types (12 and 13) involve treatment of diamines (9) with reagents such as urea, phosgene, potassium cyanate, alkyl chloroformates, dialkylcarbonate, or carbon disulfide in the presence of bases such as potassium hydroxide or potassium carbonate. Amino acids (14) or (15) can be converted to (13) via Curtius or Hoffman rearrangement on suitable derivatives such as acyl azides, hydroxyamides, or N-haloamides. Bicyclic compounds of type (16, E=sulfur or oxygen) are formed from 12 by reaction under neutral or basic conditions with alkyl halides, alkylmesylates, alkyltosylates, trialkyloxonium salts, or with an appropriate diazoalkane. Compounds of type (16; E=oxygen or sulfur) are prepared by displacement reactions using alkoxides or alkyl mecaptides with chloro intermediates as indicated.

Diamines of type 9 can be prepared by a wide variety of methods such as hydrolysis of bis-amides or amino amides, reduction of dinitro or aminonitro or hydrazino or azido groups, displacement of heteroaromatic halides or alkoxy or thio or alkylthio or hydroxy or alkyl sulfonyl groups with ammonia or amines, or rearrangement of acyl azides or amides or acids (Curtius, Hoffman, or Schmidt rearrangements). [A. S. Tomcufcik, L. N. Starker in "Heterocyclic Compounds, Pyridine and its Derivatives" Pt 3, E. Klingsberg Ed., Wiley Interscience, 1962, pp 59-62, and references cited there in; T. Nakagome in "Heterocyclic Compounds, Pyridazines" Vol. 28, R. N. Castle, Ed., Wiley Interscience, 1973, pp 597-601, and references cited therein; "Heterocyclic Compounds, The Pyrimidines" Vol. 16, D. J. Brown Ed., Wiley Interscience 1985, pp 299-325; E. Schipper, and A. R. Day *J. Am. Chem. Soc.* (1952) 74, 350; "Comprehensive Heterocyclic Chemistry," Vol. 5, A. R. Katritsky and C. W. Rees Eds., Pergamon Press 1984; pp 567-597 and 631-656 and references cited therein].

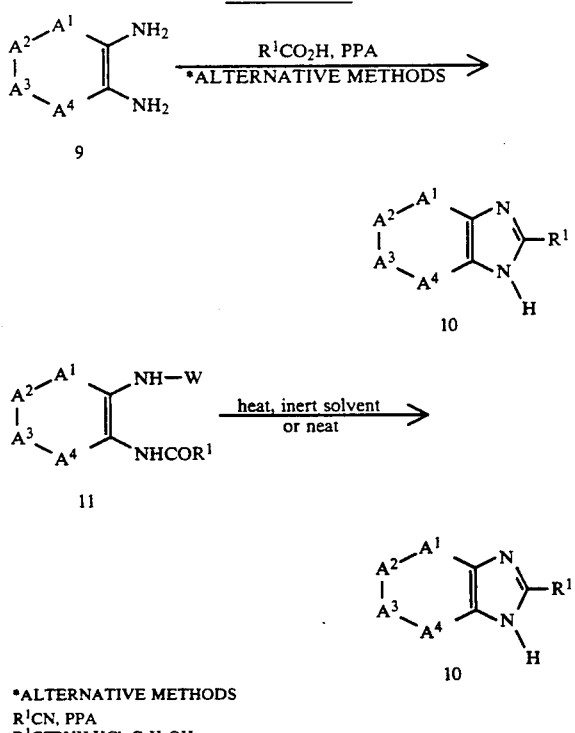

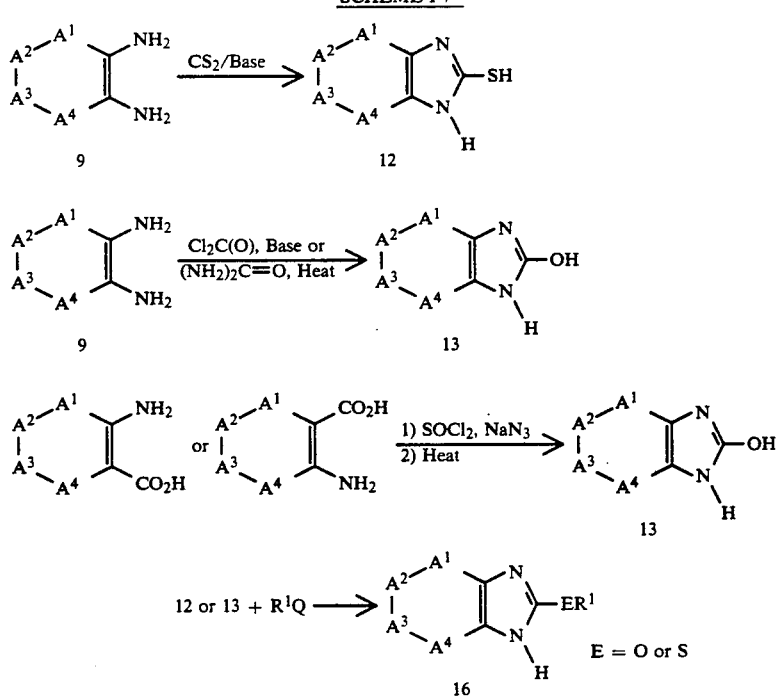

SCHEME I-7

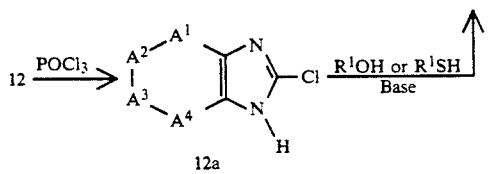

In cases wherein heterocycles of type 10 or 16 are not easily prepared from their corresponding diamines, or when these diamines cannot be prepared then alternative routes, involving fusion of the six member heterocycle onto an appropriately substituted imidazole, are used. Two of these routes are illustrated in Reaction Scheme I-8. For example, imidazo[4,5-d][1,2,3]triazines (18) are preferentially prepared by treatment of amino carboxamido imidazoles (17) with sodium nitrite in aqueous acid. Precursor imidazoles (17) are prepared by degradation of an appropriately substituted xanthine or by condensation of an appropriate imidate ester with aminocyano-acetamide. Imidazo[4,5-b]- pyridazines (20) can be prepared from imidazodi- carboxylate esters (19) by treatment with hydrazine. Oxidation of (20) gives pyridazindiones (21). The oxygen(s) in (20) or (21) can be converted to other functionalities such as halides or thiones, which are themselves precursors for the synthesis of more elaborate systems ["Comprehensive Heterocyclic Chemistry," Vol. 5, A. R. Katritsky and C. W. Rees Eds., Pergamon Press 1984; pp 567–597 and 631–656 and references cited therein].

SCHEME I-8

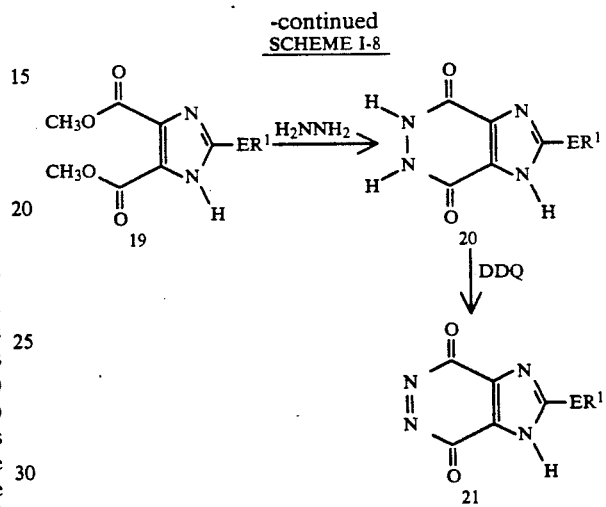

Moreover as shown in Scheme I-9 amino imidazole esters and amides are versatile intermediates for the preparation of purines. This scheme also illustrates the synthesis of the 6-membered heterocyclic ring after the alkylating agent 2 has been reacted with a suitably substituted imidazole to afford 22 or 24.

SCHEME I-9

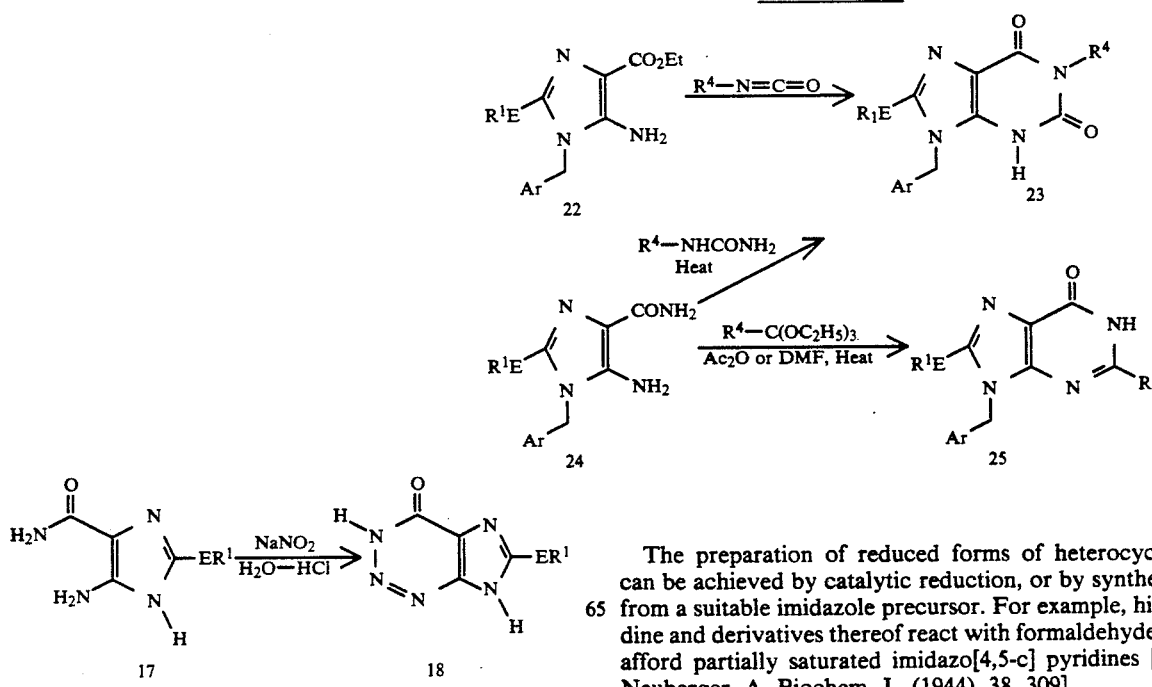

The preparation of reduced forms of heterocycles can be achieved by catalytic reduction, or by synthesis from a suitable imidazole precursor. For example, histidine and derivatives thereof react with formaldehyde to afford partially saturated imidazo[4,5-c] pyridines [cf. Neuberger, A. Biochem. J., (1944), 38, 309].

PART II

Preparation of Substituted 1,3-benzodioxole and 1,3-benzodithiole Derivatives of the General Formula I Antagonists of Formula I wherein: —$A^1$—$A^2$—$A^3$—$A^4$— is —$CR^4$=$CR^4$—$CR^4$=$CR^4$, E is a single bond to an alkyl chain, X=O or S, Y is 0, Z=$CO_2H$ and $R^6$=phenyl can be prepared as illustrated in Scheme II-1. Dichloroester 1a is stirred with neat 4-methylcatechol (X=O) at 170° C. for 10 minutes to afford ethyl 5-methyl-2-phenyl-1,3-benzodioxole-2-carboxylate, 1b (X=O, Z=$CO_2Et$). Derivative 1b where X=S and Z=$CO_2Et$ is best prepared by refluxing 3,4-dimercaptotoluene in isopropanol with 1a in the presence of $K_2CO_3$. Benzylic bromination could be carried out using NBS in refuxing $CCl_4$ with a catalytic amount of AIBN, to provide the necessary bromomethyl derivative, 1c. Deprotonation of a benzimidazole such as 2-butylbenzimidazole with strong bases such as sodium hydride or potassium t-butoxide in DMF is followed by alkyalation with bromomethyl derivative 1c to afford ester 1a. The ester is saponified with 1N NaOH to provide the free acid (1f: X=O or S).

SCHEME II-1

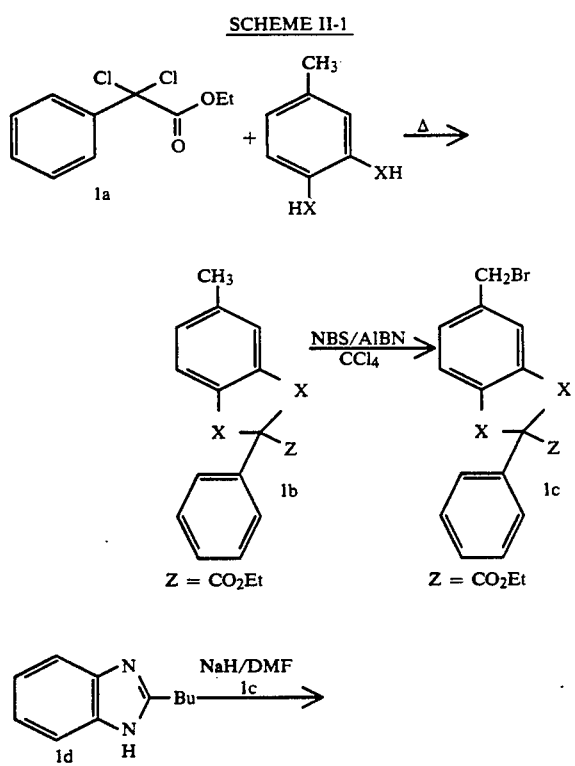

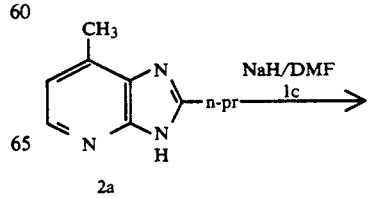

-continued
SCHEME II-1

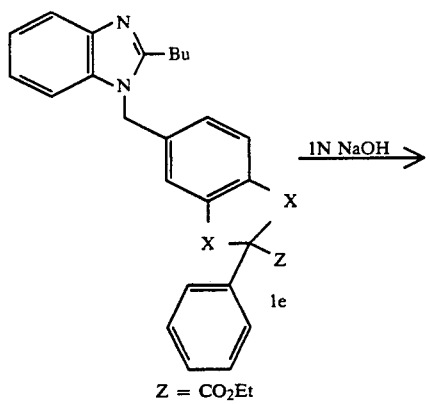

Antagonists of Formula I wherein: —$A^1$—$A^2$—$A^3$—$A^4$— is —$CR^4$=$CR^4$—$CR^4$=N—, E is a single bond to an alkyl chain, X=O or S, Y is 0, Z=$CO_2H$ and $R^6$=phenyl can be prepared as illustrated in Scheme II-2. Deprotonation of an imidazopyridine such as 7-methyl-2-propyl-imidazo[4,5-b]pyridine (2a) with strong bases such as sodium hydride or potassium t-butoxide in DMF is followed by alkylation with benzyl bromide 1c to afford ethyl ester 2b. The ester is saponified with 1N NaOH and the free acid is obtained.

SCHEME II-2

SCHEME II-2

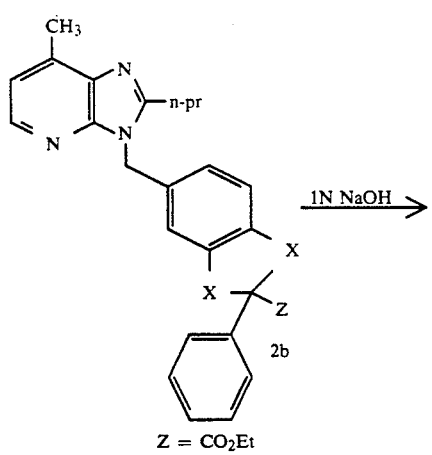

SCHEME II-3

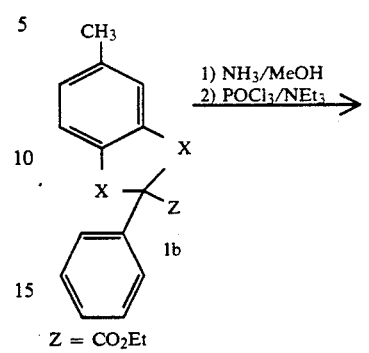

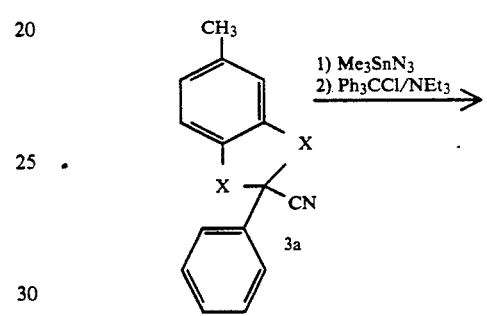

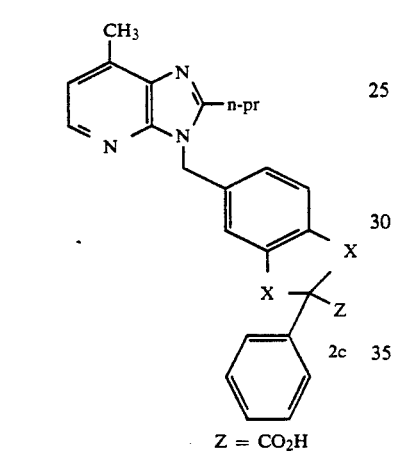

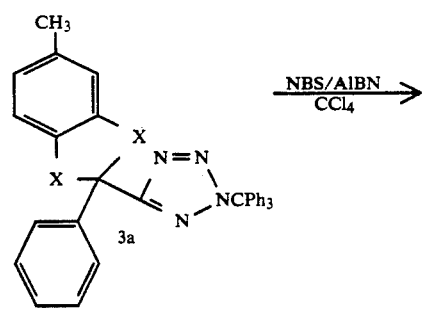

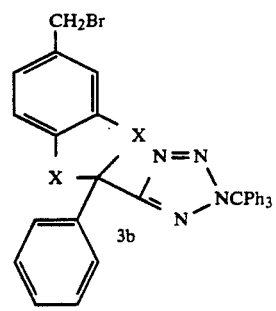

Antagonists of Formula I wherein: —$A^1$—$A^2$—$A^3$—$A^4$— is —$CR^4$=$CR^4$—$CR^4$=N—, E is a single bond to an alkyl chain, X=O or S, Y is O, Z=tetrazol-5-yl and $R^6$=phenyl can be prepared as illustrated in Scheme II-3. Ethyl 5-methyl-2-phenyl-1,3-benzodioxole-2-carboxylate or ethyl 5-methyl-2-phenyl-1,3-benzodithiole-2-carboxylate, prepared in the first step of Scheme II-1, is converted to nitrile 3a by first preparing the amide and then utilizing $POCl_3$ as a dehydrating agent. The tetrazole moiety was constructed by stirring the nitrile in toluene at reflux with $Me_3SnN_3$. The newly formed tetrazole was then protected with $Ph_3CCl/NEt_3$ to provide compound 3b. The bromomethyl derivative is then prepared using standard conditions, previously described, to afford compound 3c. Alkylation of 7-methyl-2-propyl-imidazo[4,5-b]pyridine (2a) using benzyl bromide 3c was accomplished using NaH in DMF. The trityl protecting group is easily removed with $HCl/CH_3OH$ to provide the free tetrazole, 3d (X=O or S).

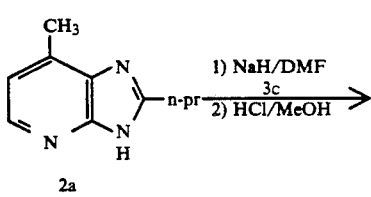

-continued
SCHEME II-3

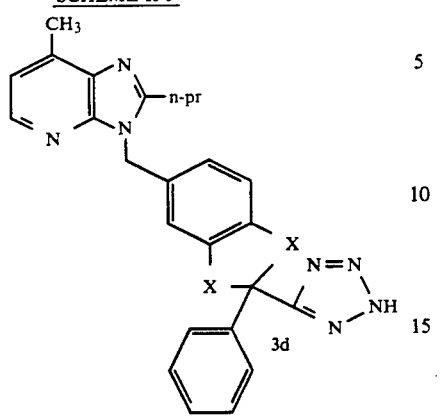

-continued
SCHEME II-4

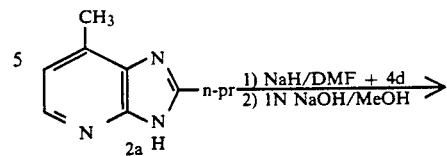

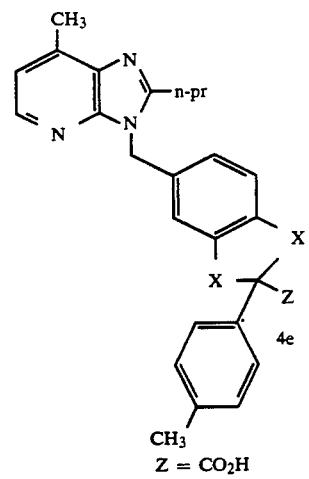

Antagonists of Formula I wherein: $-A^1-A^2-A^3-A^4-$ is $-CR^4=CR^4-CR^4=N-$, E is a single bond to an alkyl chain, X=O or S, Y is O, Z=CO$_2$H and R$^6$=p-tolyl can be prepared as illustrated in Scheme II-4. When X=S, dichloride 4a, prepared from the corresponding α-ketoester by the action of PCl$_5$ in refluxing benzene, was stirred with 3,4-dimercaptotoluene (4b: X=S) in isopropanol in the presence of K$_2$CO$_3$ to produce ethyl 5-methyl-2-(4-methyl phenyl)-1,3-benzodithiole-2-carboxylate, 4c (X=S, Z=CO$_2$Et). When X=O, 4a is reacted with 4b (X=O) neat at 170° C. for 15 minutes to afford ethyl 5-methyl-2-(4-methylphenyl)-1,3-benzodioxole-2-carboxylate, 4c (X=O, Z=CO$_2$Et). Benzylic bromination was carried out using standard conditions, NBS/AIBN in refluxing CCl$_4$, to provide the bromomethyl derivative 4d. Deprotonation of an imidazopyridine such as 7-methyl-2-propyl-imidazo[4,5-b]pyridine (2a) with strong bases such as sodium hydride or potassium t-butoxide in DMF is followed by alkylation with benzyl bromide 4d to afford the ethyl ester. The ester is saponified with 1N NaOH to afford free acid 4e.

Antagonists of Formula I wherein: $-A^1-A^2-A^3-A^4-$ is $-C(Me)=CH-C(Me)=N-$, E is a single bond to an alkyl chain, X=O or S, Y is O, Z=CO$_2$H and R$^6$=p-tolyl can be prepared as illustrated in Scheme II-5. Deprotonation of 5,7-dimethyl-2-ethyl-imidazo[4,5-b]pyridine (5a) with strong bases such as sodium hydride or potassium t-butoxide in DMF is followed by alkylation with bromomethyl derivative 4d (X=O) to afford the ethyl ester. The ester is saponified with 1N NaOH and free acid 5b is obtained.

SCHEME II-4

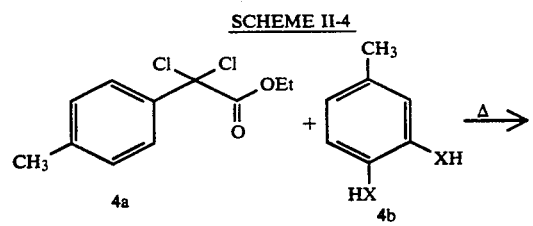

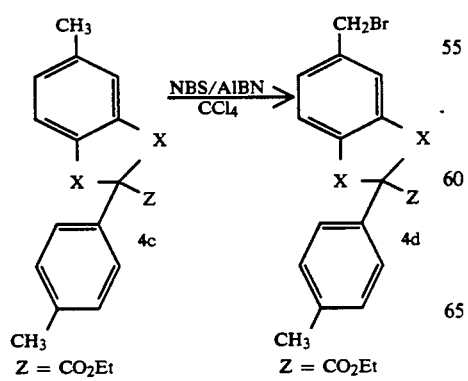

SCHEME II-5

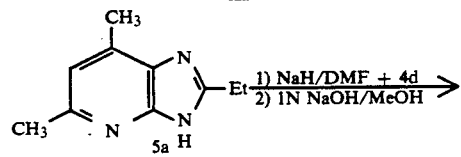

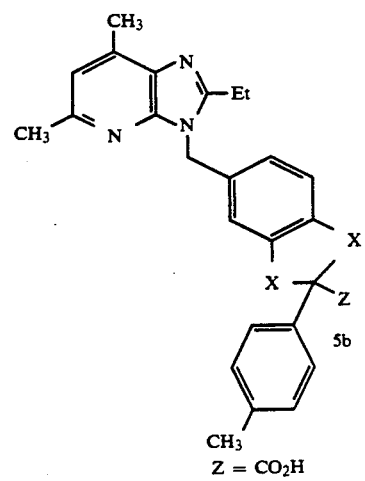

Schemes II-6 and II-7 illustrate the preparation of an A II antagonist using the second approach outlined in the section above entitled "General Methods for preparation of compounds of Formula I." In this case a heterocycle bearing a functionalized catechol substituent is prepared, and then further synthetic transformation are carried out on this intermediate. The synthesis of compound 6d of Formula Ia wherein: $-A^1=-A^2-A^3=A^4-=C(CH_3)=C(H)-C(CH_3)=N-$, B=a single bond, R1=ethyl, $R^{4b}=R^{10}=H$, $R^9$=4-(1,1,3,3-tetramethyl butane) X=O, Y=a single bond, Z=CO$_2$H and $R^{11}$=phenyl is illustrated in Scheme II-6. Deprotonation of 5,7-dimethyl-2-ethyl-imidazo[4,5-b]pyridine (5a) with strong bases such as sodium hydride or potassium t-butoxide in DMF is followed by alkylation with substituted 3,4-dimethoxy benzyl chloride 6a to provide compound 6b. Exposure of compound 6b to a variety of Lewis acids, such as BBr$_3$ or AlBr$_3$, would then uncover the catechol functionality necessary for construction of the 1,3-benzodioxole. Coupling of catechol 6c with dichloride 1a would be followed by saponification of the ethyl ester to provide acid 6d.

SCHEME II-6

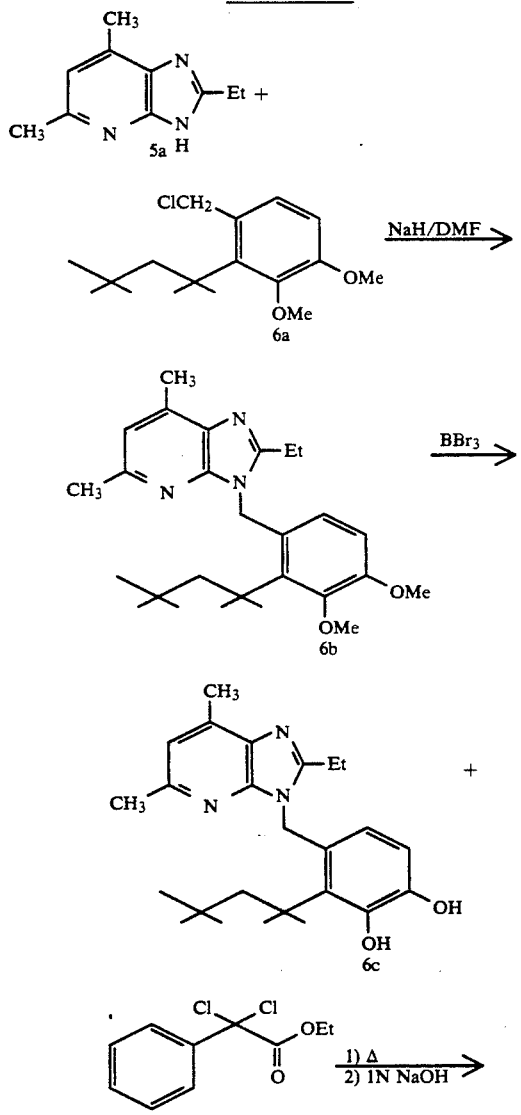

-continued
SCHEME II-6

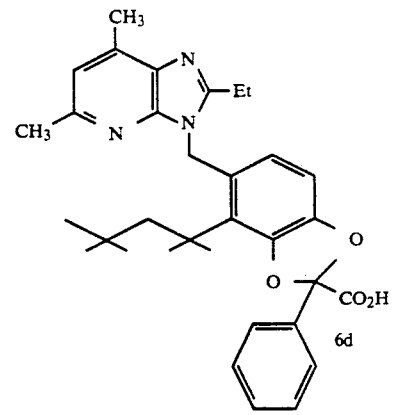

The synthesis of compound 7d of Formula Ia wherein: $A=-C(R^4)=C(R^{4b})-C(R^{4a})=N-$, B=a single bond, $R^1$=ethyl, $R^{4b}=R^{10}=H$, $R^4=R^{4a}=CH_3$, $R^9$=4-Et X=O, Y=a single bond, Z=CO$_2$H and $R^{11}$=phenyl is illustrated in Scheme II-7.

SCHEME II-7

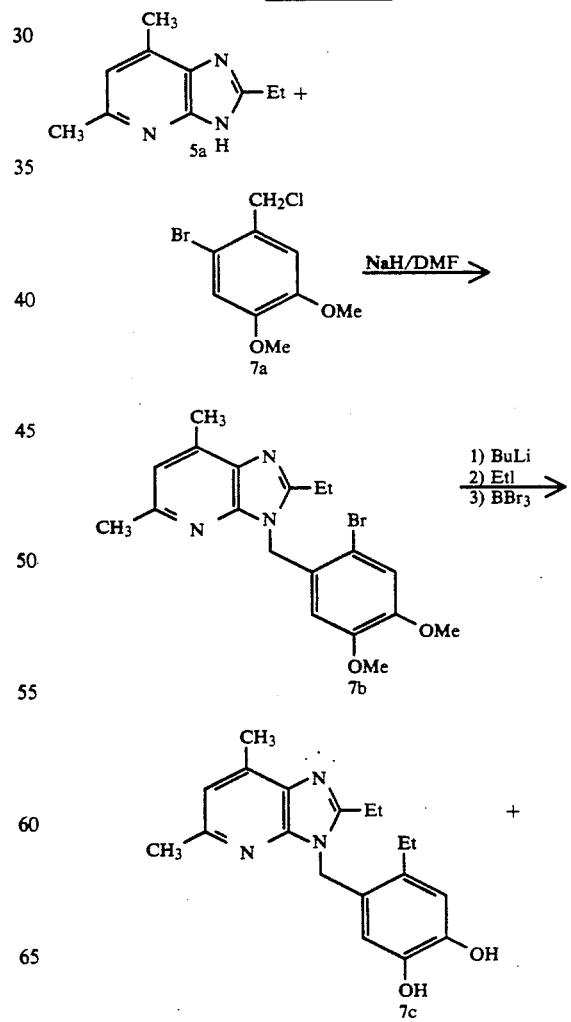

-continued
SCHEME II-7

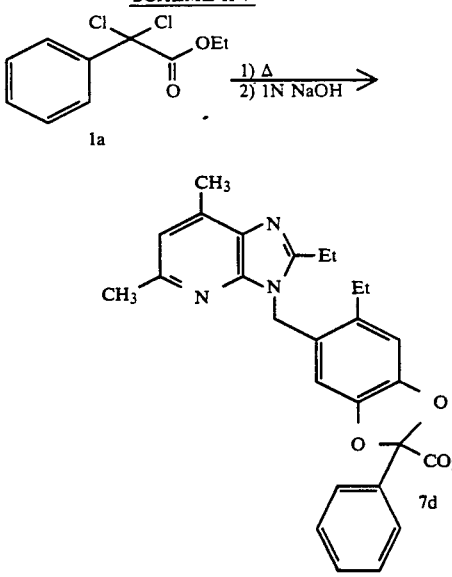

It will be appreciated by those skilled in the art that functional group transformations can be conducted on aryl and heterocyclic rings to afford desired analogs. For example, esters may be converted to amides by heating them with amines and an amide nitrogen if present in the heterocycle may be alkylated using bases such as sodium hydride in DMF with the appropriate alkyl halide. Functional group protection throughout these synthesis will be chosen to be compatible with subsequent reaction conditions. Ultimately such protecting groups will be removed to generate the desired optimally active compounds of Formula I.

The compounds of this invention form salts with various inorganic and organic acids and bases which are also within the scope of the invention. Such salts include ammonium salts, alkali metal salts like sodium and potassium salts, alkaline earth metal salts like the calcium and magnesium salts, salts with organic bases; e.g., dicyclohexylamine salts, N-methyl-D-glucamine, salts with amino acids like arginine, lysine, and the like. Also salts with organic acid inorganic acids may be prepared: e.g., HCl, HBr, $H_2SO_4$, $H_3PO_4$, methanesulfonic, toluenesulfonic, maleic, fumaric, camphorsulfonic. The non-toxic, physiologically, acceptable salts are preferred, although other salts are also useful; e.g., in isolating or purifying the product.

The salts can be formed by conventional means such as by reacting the free acid or free base forms of the product with one or more equivalents of the appropriate base or acid in a solvent or medium in which the salt is insoluble, or in a solvent such as water which is then removed in vacuo or by freeze-drying or by exchanging the cations of an existing salt for another cation on a suitable ion exchange resin.

Angiotensin II (AII) is a powerful arterial vasoconstrictor, and it exerts its action by interacting with specific receptors present on cell membranes. The compounds described in the present invention act as competitive antagonists of AII at the receptors. In order to identify AII antagonists and determine their efficacy in vitro, the following two ligand-receptor binding assays were established.

Receptor Binding Assay Using Rabbit Aortae Membrane Preparation

Three frozen rabbit aortae (obtained from Pel-Freeze Biologicals) were suspended in 5 mM Tris-0.25M Sucrose, pH 7.4 buffer (50 ml) homogenized, and then centrifuged. The mixture was filtered through a cheesecloth and the supernatant was centrifuged for 30 minutes at 20,000 rpm at 4° C. The pellet thus obtained was resuspended in 30 ml of 50 mM Tris-5 mM $MgCl_2$ buffer containing 0.2% Bovine Serum Albumin and 0.2 mg/ml Bacitracin and the suspension was used for 100 assay tubes. Samples tested for screening were done in duplicate. To the membrane preparation (0.25 ml) there was added $^{125}I$-$Sar^1$-$Ile^8$-angiotensin II [obtained from New England Nuclear] (10 ml; 20,000 cpm) with or without the test sample and the mixture was incubated at 37° C. for 90 minutes. The mixture was then diluted with ice-cold 50 mM Tris-0.9% NaCl, pH 7.4 (4 ml) and filtered through a glass fiber filter (GF/B Whatman 2.4" diameter). The filter was soaked in scintillation cocktail (10 ml) and counted for radioactivity using Packard 2660 Tricarb liquid scintillation counter. The inhibitory concentration ($IC_{50}$) of potential AII antagonist which gives 50% displacement of the total specifically bound $^{125}I$-$Sar^1Ile^8$-angiotensin II was presented as a measure of the efficacy of such compounds as AII antagonists.

Receptor Assay Using Bovine Adrenal Cortex Preparation

Bovine adrenal cortex was selected as the source of AII receptor. Weighed tissue (0.1 g is needed for 100 assay tubes) was suspended in Tris.HCl (50 mM), pH 7.7 buffer and homogenized. The homogenate was centrifuged at 20,000 rpm for 15 minutes. Supernatant was discarded and pellets resuspended in buffer [$Na_2HPO_4$ (10 mM)-NaCl (120 mM)-disodium EDTA (5 mM) containing phenylmethane sulfonyl fluoride (PMSF)(0.1 mM)]. (For screening of compounds, generally duplicates of tubes are used). To the membrane preparation (0.5 ml) there was added 3H-angiotensin II (50 mM) (10 ml) with or without the test sample and the mixture was incubated at 37° C. for 1 hour. The mixture was then diluted with Tris buffer (4 ml) and filtered through a glass fiber filter (GF/B Whatman 2.4" diameter). The filter was soaked in scintillation cocktail (10 ml) and counted for radioactivity using Packard 2660 Tricarb liquid scintillation counter. The inhibitory concentration ($IC_{50}$) of potential AII antagonist which gives 50% displacement of the total specifically bound 3H-angiotensin II was presented as a measure of the efficacy of such compounds as AII antagonists.

Using the methodology described above, representative compounds of the invention were evaluated and were found to exhibit an activity of at least $IC_{50} < 50$ mM thereby demonstrating and confirming the utility of the compounds of the invention as effective AII antagonists.

The potential antihypertensive effects of the compounds described in the present invention may be evaluated using the methodology described below:

Male Charles River Sprague-Dawley rats (300–375 gm) were anesthetized with methohexital (Brevital; 50 mg/kg i.p.). The trachea was cannulated with PE 205 tubing. A stainless steel pithing rod (1.5 mm thick, 150 mm long) was inserted into the orbit or the right eye and down the spinal column. The rats were immediately placed on a Harvard Rodent Ventilator (rate—60 strokes per minute, volumn—1.1 cc per 100 grams body weight). The right carotid artery was ligated, both left and right vagal nerves were cut, the left carotid artery was cannulated with PE 50 tubing for drug administration, and body temperature was maintained at 37° C. by a thermostatically controlled heating pad which received input from a rectal temperature probe. Atropine (1 mg/kg i.v.) was then administered and 15 minutes later propranolol (1 mg/kg i.v.). Thirty minutes later antagonists of formula I were administered intravenously or orally. Angiotensin II was then typically given at 5, 10, 15, 30, 45 and 60 minute intervals and every half-hour thereafter for as long as the test compound showed activity. The change in the mean arterial blood pressure was recorded for each angiotensin II challenge and the percent inhibition of the angiotensin II response was calculated.

Thus, the compounds of the invention are useful in treating hypertension. They are also of value in the management of acute and chronic congestive heart failure. These compounds may also be expected to be useful in the treatment of secondary hyperaldosteronism, primary and secondary pulmonary hyperaldosteronism, primary and secondary pulmonary hypertension, renal failure, such as diabetic nephropathy, glomerulonephritis, scleroderma, glomerular sclerosis, proteinuria of primary renal disease, end stage renal disease, renal transplant therapy, and the like, renal vascular hypertension, left ventricular dysfunction, diabetic retinapathy and in the management of vascular disorders such as migraine, Raynaud's disease, luminala hyperclasia, and to minimize the atherosclerotic process. The application of the compounds of this invention for these and similar disorders will be apparent to those skilled in the art.

The compounds of this invention are also useful to treat elevated intraocular pressure and to enhance retinal blood flow and can be administered to patients in need of such treatment with typical pharmaceutical formulations such as tablets, capsules, injectables and the like as well as topical ocular formulations in the form of solutions, ointments, inserts, gels, and the like. Pharmaceutical formulations prepared to treat intraocular pressure would typically contain about 0.1% to 15% by weight, preferably 0.5% to 2% by weight, of a compound of this invention.

In the management of hypertension and the clinical conditions noted above, the compounds of this invention may be utilized in compositions such as tablets, capsules or elixirs for oral administration, suppositories for rectal administration, sterile solutions or suspensions for parenteral or intramuscular administration, and the like. The compounds of this invention can be administered to patients (animals and human) in need of such treatment in dosages that will provide optimal pharmaceutical efficacy. Although the dose will vary from patient to patient depending upon the nature and severity of disease, the patient's weight, special diets then being followed by a patient, concurrent medication, and other factors which those skilled in the art will recognize, the dosage range will generally be about 1 to 1000 mg. per patient per day which can be administered in single or multiple doses. Perferably, the dosage range will be about 2.5 to 250 mg. per patient per day; more preferably about 2.5 to 75 mg. per patient per day.

The compounds of this invention can also be administered in combination with other antihypertensives and/or diuretics and/or angiotensin converting enzyme inhibitors and/or calcium channel blockers. For example, the compounds of this invention can be given in combination with such compounds as amiloride, atenolol, bendroflumethiazide, chlorothalidone, chlorothiazide, clonidine, cryptenamine acetates and cryptenamine tannates, deserpidine, diazoxide, guanethidene sulfate, hydralazine hydrochloride, hydrochlorothiazide, metolazone, metoprolol tartate, methyclothiazide, methyldopa, methyldopate hydrochloride, minoxidil, pargyline hydrochloride, polythiazide, prazosin, propranolol, *rauwolfia serpentina,* rescinnamine, reserpine, sodium nitroprusside, spironolactone, timolol maleate, trichloromethiazide, trimethophan camsylate, benzthiazide, quinethazone, ticrynafan, triamterene, acetazolamide, aminophylline, cyclothiazide, ethacrynic acid, furosemide, merethoxylline, procaine, sodium ethacrynate, captopril, delapril hydrochloride, enalapril, enalaprilat, fosinopril sodium, lisinopril, pentopril, quinapril hydrochloride, ramapril, teprotide, zofenopril calcium, diflusinal, diltiazem, felodipine, nicardipine, nifedipine, niludipine, nimodipine, nisoldipine, nitrendipine, and the like, as well as admixtures and combinations thereof.

Typically, the individual daily dosages for these combinations can range from about one-fifth of the minimally recommended clinical dosages to the maximum recommended levels for the entities when they are given singly.

To illustrate these combinations, one of the angiotensin II antagonists of this invention effective clinically in the 2.5-250 milligrams per day range can be effectively combined at levels at the 0.5-250 milligrams per day range with the following compounds at the indicated per day dose range: hydrochlorothiazide (15-200 mg) chlorothiazide (125-2000 mg), ethacrynic acid (15-200 mg), amiloride (5-20 mg), furosemide (5-80 mg), propranolol (20-480 mg), timolol maleate (5-60 mg.), methyldopa (65-2000 mg), felodipine (5-60 mg), nifedipine (5-60 mg), and nitrendipine (5-60 mg). In addition, triple drug combinations of hydrochlorothiazide (15-200 mg) plus amiloride (5-20 mg) plus angiotensin II antagonist of this invention (3-200 mg) or hydrochlorothiazide (15-200 mg) plus timolol maleate (5-60) plus an angiotensin II antagonist of this invention (0.5-250 mg) or hydrochlorothiazide (15-200 mg) and nifedipine (5-60 mg) plus an angiotensin II antagonist of this invention (0.5-250 mg) are effective combinations to control blood pressure in hypertensive patients. Naturally, these dose ranges can be adjusted on a unit basis as necessary to permit divided daily dosage and, as noted above, the dose will vary depending on the nature and severity of the disease, weight of patient, special diets and other factors.

Typically, these combinations can be formulated into pharmaceutical compositions as discussed below.

About 1 to 100 mg. of compound or mixture of compounds of Formula I or a physiologically acceptable salt is compounded with a physiologically acceptable vehicle, carrier, excipient, binder, preservative, stabilizer, flavor, etc., in a unit dosage form as called for by accepted pharmaceutical practice. The amount of active substance in these compositions or preparations is such that a suitable dosage in the range indicated is obtained.

Illustrative of the adjuvants which can be incorporated in tablets, capsules and the like are the following: a binder such as gum tragacanth, acacia, corn starch or gelatin; an excipient such as microcrystalline cellulose; a disintegrating agent such as corn starch, pregelatinized starch, alginic acid and the like; a lubricant such as magnesium stearate; a sweetening agent such as sucrose, lactose or saccharin; a flavoring agent such as peppermint, oil or wintergreen or cherry. When the dosage unitform is a capsule, it may contain, in addition to materials of the above type, a liquid carrier such as fatty oil. Various other materials may be present as coatings or to otherwise modify the physical form of the dosage unit. For instance, tablets may be coated with shellac, sugar or both. A syrup or elixir may contain the active compound, sucrose as a sweetening agent, methyl and propyl parabens as preservatives, a dye and a flavoring such as cherry or orange flavor.

Sterile compositions for injection can be formulated according to conventional pharmaceutical practice by dissolving or suspending the active substance in a vehicle such as water for injection, a naturally occuring vegetable oil like sesame oil, coconut oil, peanut oil, cottonseed oil, etc., or a synthetic fatty vehicle like ethyl oleate or the like. Buffers, preservatives, antioxidants and the like can be incorporated as required.

The compounds of this invention are also useful to treat elevated intraocular pressure and can be administered to patients in need of such treatment with typical pharmaceutical formulations such as tablets, capsules, injectables, as well as topical ocular formulations in the form of solutions, ointments, inserts, gels and the like. Pharmaceutical formulations prepared to treat intraocular pressure would typically contain about 0.1% to 15% by weight, and preferably 0.5% to 2.0% by weight of a compound of this invention.

Thus, the compounds of the invention are useful in treating hypertension. They are also of value in the management of acute and chronic congestive heart failure, in the treatment of secondary hyperaldosteronism, primary and secondary pulmonary hypertension, renal failure such as diabetic nephropathy, glomerulonephritis, scleroderma, and the like, renal vascular hypertension, left ventricular dysfunction, diabetic retinopathy, and in the management of vascular disorder such as migraine or Raynaud's disease. The application of the compounds of this invention for these and similar disorders will be apparent to those skilled in the art.

The useful central nervous system (CNS) activities of the compounds of this invention are demonstrated and exemplified by the ensuing assays.

COGNITIVE FUNCTION ASSAY

The efficacy of these compounds to enhance cognitive function can be demonstrated in a rat passive avoidance assay in which cholinomimetics such as physostigmine and nootropic agents are known to be active. In this assay, rats are trained to inhibit their natural tendency to enter dark areas. The test apparatus used consists of two chambers, one of which is brightly illuminated and the other is dark. Rats are placed in the illuminated chamber and the elapsed time it takes for them to enter the darkened chamber is recorded. On entering the dark chamber, they receive a brief electric shock to the feet. The test animals are pretreated with 0.2 mg/kg of the muscarinic antagonist scopolamine which disrupts learning or are treated with scopolamine and the compound which is to be tested for possible reversal of the scopolamine effect. Twenty-four hours later, the rats are returned to the illuminated chamber. Upon return to the illuminated chamber, normal young rats who have been subjected to this training and who have been treated only with control vehicle take longer to re-enter the dark chamber than test animals who have been exposed to the apparatus but who have not received a shock. Rats treated with scopolamine before training do not show this hesitation when tested 24 hours later. Efficacious test compounds can overcome the disruptive effect on learning which scopolamine produces. Typically, compounds of this invention should be efficacious in this passive avoidance assay in the dose range of from about 0.1 mg/kg to about 100 mg/kg.

ANXIOLYTIC ASSAY

The anxiolytic activity of the invention compounds can be demonstrated in a conditioned emotional response (CER) assay. Diazepam is a clinically useful anxiolytic which is active in this assay. In the CER protocol, male Sprague-Dawley rats (250–350 g) are trained to press a lever on a variable interval (VI) 60 second schedule for food reinforcement in a standard operant chamber over weekly (five days per week) training sessions. All animals then receive daily 20 minute conditioning sessions, each session partitioned into alternating 5 minute light (L) and 2 minute dark (D) periods in a fixed L1D1L2D2L3 sequence. During both periods (L or D), pressing a lever delivers food pellets on a VI 60 second schedule: in the dark (D), lever presses also elicit mild footshock (0.8 mA, 0.5 sec) on an independent shock presentation schedule of VI 20 seconds. Lever pressing is suppressed during the dark periods reflecting the formation of a conditioned emotional response (CER).

Drug testing in this paradigm is carried out under extinction conditions. During extinction, animals learn that responding for food in the dark is no longer punished by shock. Therefore, response rates gradually increase in the dark periods and animals treated with an anxiolytic drug show a more rapid increase in response rate than vehicle treated animals. Compounds of this invention should be efficacious in this test procedure in the range of from about 0.1 mg/kg to about 100 mg/kg.

DEPRESSION ASSAY

The antidepressant activity of the compounds of this invention can be demonstrated in a tail suspension test using mice. A clinically useful antidepressant which serves as a positive control in this assay is desipramine. The method is based on the observations that a mouse suspended by the tail shows alternate periods of agitation and immobility and that antidepressants modify the balance between these two forms of behavior in favor agitation. Periods of immobility in a 5 minute test period are recorded using a keypad linked to a microcomputer which allows the experimenter to assign to each animal an identity code and to measure latency, duration and frequency of immobile periods. Compounds of this invention should be efficacious in this test procedure in the range of from about 0.1 mg/kg to about 100 mg/kg.

SCHIZOPHRENIA ASSAY

The antidopaminergic activity of the compounds of this invention can be demonstrated in an apomorphine-induced sterotypy model. A clinically useful antipsychotic drug that is used as a positive control in this assay is haloperidol. The assay method is based upon the observation that stimulation of the dopaminergic system in rats produces stereotyped motor behavior. There is a strong correlation between the effectiveness of classical neuroleptic drugs to block apomorphine-induced stereotypy and to prevent schizophrenic symptoms. Stereotyped behavior induced by apomorphine, with and without pretreatment with test compounds, is recorded using a keypad linked to a microcomputer. Compounds of the invention should be efficacious in this assay in the range of from about 0.1 mg/kg to about 100 mg/kg.

In the treatment of the clinical condition noted above, the compounds of this invention may be utilized in compositions such as tablets, capsules or elixirs for oral administration, suppositories for rectal administration, sterile solutions or suspensions for parenteral or intramuscular administration, and the like. The compounds of this invention can be administered to patients (animals and human) in need of such treatment in dosages that will provide optimal pharmaceutical efficacy. Although the dose will vary from patient to patient depending upon the nature and severity of disease, the patient's weight, special diets then being followed by a patient, concurrent medication, and other factors which those skilled in the art will recognize, the dosage range will generally be about 5 to 6000 mg. per patient per day which can be administered in single or multiple doses. Perferably, the dosage range will be about 10 to 4000 mg. per patient per day; more preferably about 20 to 2000 mg per patient per day.

In order to obtain maximal enhancement of cognitive function, the compounds of this invention may be combined with other cognition-enhancing agents. These include acetylcholin- esterase inhibitors such as heptylphysostigmine and tetrahydro-acridine (THA; tacrine), muscarinic agonists such as oxotremorine, inhibitors of angiotensin-converting enzyme such as octylramipril, captopril, ceranapril, enalapril, lisinopril, fosinopril and zofenopril, centrally-acting calcium channel blockers and as nimodipine, and nootropic agents such as piracetam.

In order to achieve optimal anxiolytic activity, the compounds of this invention may be combined with other anxiolytic agents such as alprazolam, lorazepam, diazepam, and busipirone.

In order to achieve optimal antidepressant activity, combinations of the compounds of this invention with other antidepressants are of use. These include tricyclic antidepressants such as nortriptyline, amitryptyline and trazodone, and monoamine oxidase inhibitors such as tranylcypromine.

In order to obtain maximal antipsychotic activity, the compounds of this invention may be combined with other antipsychotic agents such as promethazine, fluphenazine and haloperidol.

The following examples illustrate the preparation of the compounds of Formula I and their incorporation into pharmaceutical compositions and as such are not to be considered nor construed as limiting the invention set forth in the claims appended hereto.

EXAMPLE 1

5-[1-(2-butylbenzimidazolyl)]-2-phenyl-1,3-benzodioxole-2-carboxylic acid (compound 1f of scheme II-1 where X=O, and Z=CO$_2$H)

Step A: Preparation of Ethyl 5-methyl-2-phenyl-1,3-benzodioxole-2-carboxylate (scheme II-1, compound 1b where X=O)

To a solution of ethyl benzoylformate (520 mg, 2.92 mmoL) in dry benzene 5 mL) was added PCl$_5$ (608 mg, 1.0 equiv). After stirring at reflux for 16 h TLC analysis indicated that all the starting material appeared consumed. The solvent was removed in vacuo and the crude dichloride (Rf=0.61 6:1 hexane/ethyl acetate) was mixed with 4-methyl-catechol (724 mg 2.0 equiv) and heated to 175° C. until HCl evolution ceased (ca. 20 min). The mixture was cooled to rt and the glue-like material was dissolved in diethyl ether and washed several times with 1N NaOH and then brine. The organic was dried over anhydrous MgSO$_4$ and concentrated in vacuo and the residue was chromatographed on a silica column eluting with hexane/ethyl acetate (20:1). Removal of the solvent afforded 130 mg (16%) of the titled compound. Rf=0.57 (6:1 hexane/ethyl acetate).

1H NMR (300 MHz, CDCl$_3$) δ1.21 (t, 3H), 2.29 (s, 3H), 4.26 (q, 2H), 6.66 (d, 1H), 6.78 (s, 1H), 6.82 (d, 1H), 7.42 (m, 3H), 7.71 (m, 2H).

Step B: Preparation of Ethyl 5-bromomethyl-2-phenyl-1,3-benzodioxole-2-carboxylate (scheme II-1, compound 1c where X=O)

To a solution of the product of Step A (130 mg, 0.458 mmoL) in dry CCl$_4$ (3mL) was added NBS (82 mg, 1.0 equiv) and a catalytic amount of benzoylperoxide. The mixture was stirred at reflux under N$_2$ and monitored by TLC. After 1 h TLC analysis indicated that the reaction had gone to completion. The now cooled reaction mixture was diluted with diethyl ether and filtered through a plug of cotton. The filtrate was concentrated and the residue was chromatographed on a silica column eluting with hexane/ethyl acetate (20:1). Removal of the solvent afforded 157 mg (94%) of the titled compound. RF=0.51 (6:1 hexane/ethyl acetate).

1H NMR (300 MHz, CDCl$_3$) δ1.25 (t, 3H), 4.27 (q, 2H), 4.42 (s, 2H), 6.88 (q, 2H), 6.98 (s, 1H), 7.42 (m, 3H), 7.70 (m, 2H).

Step C: Preparation of Ethyl 5-[1-(2-butyl-benzimidazolyl]-2-phenyl-1,3-benzodioxole-2-carboxylate (compound 1e of Scheme II-1, where X=O)

To a solution of 2-butylbenzimidazole (36 mg, 0.207 mmoL), prepared according to the procedures described in EP 400,835, pub. date Dec. 5, 1990, (1 mL) was added 60% NaH in oil (8.3 mg, 1 equiv). After stirring under N$_2$ for 1 h a solution of the product of Step B (38 mg, 0.104 mmoL) in dry DMF (1 mL) was added. After 1 h the reaction was quenched with sat'd NH$_4$Cl soln and the DMF was removed under high vacuum. The residue was taken up in ethyl acetate and washed with brine, dried over anhydrous MgSO$_4$ and concentrated in vacuo. The residue was purified by flash chromatography eluting with hexane/ethyl acetate (1.5:1) to afford, after removal of solvent, 13.5 mg (28%) of the titled compound. RF=0.51 (2:1 ethyl acetate/hexane).

1H NMR (300 MHz, CDCl$_3$) δ0.93 (t, 3H), 1.23 (t, 3H), 1.41 (m, 2H), 1.83 (m, 2H), 4.22 (q, 2H), 5.22 (s, 2H), 6.56 (d, 1H), 6.72 (s, 1H), 6.83 (d, 1H), 7.18–7.26 (comp m, 3H), 7.41 (m, 3H), 7.65 (dd, 2H), 7.76 (d, 1H).

Step D: Preparation of 5-[1-(2-butylbenzimidazolyl)]-2-phenyl-1,3-benzodioxole-2-carboxylic acid (compound 1f of Scheme II-1 where X=O)

To a solution of the product of Step C in CH$_3$OH was added 1N NaOH until the solution begins to turn cloudy. After 3 h at rt the reaction was complete. The CH$_3$OH was removed in vacuo and the residue was taken up in CH$_2$Cl$_2$ and washed with pH 6 solution and

EXAMPLE 2

5-[3'-(7'-methyl-2'-propyl imidazo[4,5-b]pyridinyl)]-2 2-phenyl-1,3-benzodioxole-2-carboxylic acid (compound 2c of Scheme II-2 where X=O, and Z=CO₂H)

Step A: Preparation of Ethyl 5-[3'-(7'-methyl-2'-propylimidazo-[4,5-b]pyridinyl)]-2phenyl-1,3-benzodioxole-2-carboxylate (compound 2b of Scheme II-2, where X=O)

To a solution of 7-methyl-2-propylimidazopyridine (36 mg 0.206 mmoL), prepared according to the procedures described in EP 400,974 pub. date Dec. 5, 1990, in dry DMF (1 mL) was added 60% NaH in oil (8.3 mg, 1 equiv). After 30 min a solution of the product of Step B, Example 1 (37 mg, 0.102 mmoL) in DMF (1 mL) was added. After 15 min the reaction was quenched with a sat'd soln of NH₄Cl and the DMF was removed under high vacuum. The residue was taken up in ethyl acetate, washed with H₂O and brine, dried over anhyudrous MgSO₄ and concentrated in vacuo. The residue was purified by flash chromatography eluting with ethyl acetate/hexane (2:1) to provide 10.5 mg (23% of the titled compound. Rf=0.50 (10:1 ethyl acetate/hexane).

1H NMR (300 MHz, CDCl₃) δ0.98 (t, 3H), 1.21 (t, 3H), 1.78 (m, 2H), 2.69 (s, 3H), 2.78 (t, 2H), 4.22 (q, 2H), 5.39 (s, 2H), 6.68 (d, 1H), 6.75 (s, 1H), 6.82 (d, 1H), 7.02 (d, 1H), 7.41 (m, 3H), 7.67 (dd, 2H), 8.20 (d, 1H).

Step B: Preparation of 5-[3'-(7'-methyl-2'-propylimidazo[4,5-b]pyridinyl)]-2-phenyl-1,3-benzodioxole-2-carboxylic acid (compound 2c of Scheme II-2, where X=O)

To a solution of the product of Step A (10.5 mg, 0.023 mmoL) in CH3OH (1mL) was added 1N NaOH (0.025 mL, 1.1 equiv). After stirring for 3 h at 30° C. the reaction had appeared to have gone to completion by TLC analysis. The solvent was removed in vacuo and the residue was concentrated from benzene several times to obtain the dry sodium salt of the titled compound (9.8 mg, 95%). RF=0.33 (100:20:1 CH₂Cl₂/CH₃OH/NH₄OH, twice).

1H NMR (300 MHz, CD₃OD) δ0.91 (t, 3H), 1.68 (m, 2H), 2.62 (s, 3H), 2.82 (t, 2H), 5.41 (s, 2H), 6.61 (d, 1H), 6.69 (s, 1H), 6.78 (d, 1H), 7.11 (d, 1H), 7.31 (m, 3H), 7.62 (dd, 2H), 8.17 (d, 1H).

EXAMPLE 3

Ethyl 5-[3'-(7'-methyl-2-propylimidazo[4,5-b]pyridinyl)]-2-phenyl-1,3-benzodithiole-2-carboxylate (compound 2c where X=S and Z=CO₂H)

Step A: Preparation of Ethyl 5-methyl-2-phenyl-1,3-benzodithiole-2-carboxylate (scheme II-1, compound 1b where X=S)

To a solution of ethyl benzoylformate (1.53 g, 8.59 mmoL) in benzene (10 mL) under N₂ was added PCl₅ (2.58 g, 1.5 equiv). After stirring at reflux for 6 h the mixture was concentrated down and diluted with diethyl ether. The organic was washed with H₂O and brine, dried over MgSO₄ and concentrated in vacuo to afford 1.92 g of crude dichloride. In a separate flask a solution of 3,4-dimercaptotoluene (350 mg, 2.24 mmoL) in isopropanol (5 mL) was added K₂CO₃ (1.5 g, 5 equiv) and a portion of the dichloride (200 mg 0.86 mmoL). The reaction was stirred at reflux under N₂ for 24 h and then the isopropanol was removed under a stream of N₂. The residue was diluted with diethyl ether, washed with H₂O and brine, dried over anhydrous MgSO₄ and concentrated in vacuo. The product was purified by flash chromatography eluting with hexane/ethyl acetate (25:1) to afford 242 mg of the titled compound. Rf=0.52 (6:1 hexane/ethyl acetate).

1H NMR (250 MHz, CDCl₃) δ1.23 (t, 3H), 2.25 (s, 3H), 4.23 (q, 2H), 6.73 (d, 1H), 7.05 (s, 1H), 7.09 (d, 1H), 7.31 (m, 3H), 7.72 (dd, 2H).

Step B: Preparation of Ethyl 5-bromomethyl-2-phenyl-1,3-benzodithiole-2-carboxylate (scheme II-1, compound 1c where X=S)

To a solution of the product of Step A (54 mg, 0.171 mmoL) in dry CCl₄ (5mL) was added NBS (27 mg, 0.9 equiv) and a catalytic amount of AlBN. The mixture was refuxed under N₂ for 2 h. The mixture was cooled to rt, diluted with diethyl ether and filtered. The filtrate was concentrated in vacuo and the residue was purified by flash chromatography eluting with hexane/ethyl acetate (25:1) to afford 52 mg (77%) of the titled compound. RF=0.55 (6:1 hexane/ethyl acetate).

1H NMR (300 MHz, CDCl₃) δ1.22 (t, 3H), 4.25 (q, 2H), 4.39 (s, 2H), 7.03 (d, 1H), 7.15 (d, 1H), 7.22 (s, 1H), 7.32 (m, 3H), 7.72 (d, 2H).

Step C: Preparation of Ethyl 5-[3'-(7'-methyl-2-propylimidazo[4,5-b]pyridinyl)]-2-phenyl-1,3-benzodithiole-2-carboxylate (compound 2b of Scheme II-2 where X=S)

The titled compound was prepared from the product of Step B utilizing the same procedure used to prepare the product of Example 2, Step A, Rf=0.23 (2:1 hexane/ethyl acetate).

1H NMR (250 MHz, CDCl₃) δ0.98 (t, 3H), 1.21 (t, 3H), 1.77 (m, 2H), 2.69 (s, 3H), 2.76 (t, 2H), 4.21 (q, 2H), 5.38 (s, 2H), 6.79 (d, 1H), 6.96 (s, 1H), 7.02 (d, 1H), 7.11 (d, 1H), 7.31 (m, 3H), 7.65 (dd, 2H), 8.19 (d, 1H).

Step D: Preparation of 5-[3'-(7'-methyl-2-propylimidzopyridinyl)]-2-phenyl-1,3-benzodithiole-2-carboxylic acid (compound 2c of Scheme II-2 where X=S)

The titled compound was prepared from the product of Step C utilizing the same procedure used to prepare the product of example 2, Step B. Rf=0.12 (100:10:1 CH₂Cl₂/CH₃OH/NH₄OH).

1H NMR (250 MHz, CD₃OD) δ0.85 (t, 3H), 1.61 (m, 2H), 2.61 (s, 3H), 2.78 (t, 2H), 5.41 (s, 2H), 6.70 (d, 1H), 6.95 (s, 1H), 7.08 (d, 1H), 7.12–7.28 (comp m, 4H), 7.80 (dd, 2H), 8.14 (d, 1H).

EXAMPLE 4

2-(1'H-tetrazol-5'-yl)-5-[3"-(7"-methyl-2"propylimidazo-[4,5-b]pyridinyl)]-2-phenyl-1,3-benzodioxole (Scheme II-3, compound 3d where X=O)

Step A: Preparation of 2-cyano-5-methyl-2-phenyl-1,3-benzodithiole (scheme II-3, compound 3a where X=O)

To a solution of ethyl 5-methyl-2-phenyl-1,3-benzodioxole-2-carboxylate (317 mg, 1.12 mmoL) in dry CH₃OH cooled to 0° C. was bubbled in NH₃ gas for ca. 2 h. After 2.5 h the solvent was removed in vacuo to provide the carboxamide (260 mg, 92%). The carboxamide was dissolved in POCl$_3$ (3 mL) was the mixture cooled to 0° C. under N$_2$. To this mixture was added NEt$_3$ (0.300 mL, 2.2 equiv) very slowly throughout 25 min. After the addition the reaction was allowed to stir at rf for 30 min. The mixture was then refluxed for 35 min. The reaction was taken up in diethyl ether/toluene and washed twice with 1N NaOH and finally with brine. The organic was dried over anhydrous MgSO$_4$ and concentrated in vacuo. The residue was purified by flash chromatography eluting with hexane/ethyl acetate (25:1) to afford 169 mg of the titled compound. Rf=0.77 (2:1 hexane/ethyl acetate).

1H NMR (300 MHz, CDCl$_3$) δ2.32 (s, 3H), 6.78 (d, 1H), 6.82 (s, 1H), 6.88 (d, 1H), 7.53 (m, 3H), 7.81 (d, 2H).

Step B: Preparation of 2-(1-triphenylmethyltetrazol-5-yl)-5-methyl-2-phenyl-1,3-benzodioxole (compound 3b where X=O)

To a solution of the product of Step A (169 mg, 0.713 mmoL) dissolved in toluene (10 mL) under N$_2$ was added Me$_3$SnN$_3$ (292 mg, 2 equiv). The reaction was stirred at reflux for 4 h. After cooling to rt the mixture was diluted with diethyl ether/ethyl acetate and washed with NH$_4$Cl soln and brine. The organic was dried over anhydrous MgSO$_4$ and concentrated in vacuo to afford 158 mg (77%) of the free tetrazole derivative. The tetrazole was dissolved in CH$_2$Cl$_2$ (2.5 mL) under N$_2$ and NEt$_3$ (0.152 mL, 2 equiv) and trityl chloride (183 mg, 1.2 equiv) were added. After stirring at rt for 1.5 h the mixture was diluted with ethyl acetate and washed with H$_2$O and brine. The organic was dried over anhydrous MgSO$_4$ and concentrated in vacuo. The residue was purified by flash chromatography eluting with hexane/ethyl acetate (20:1) to afford 215 mg (75%) of the titled compound. Rf=0.37 (15:1 hexane/ethyl acetate 2x's).

1H NMR (300 MHz, CDCl$_3$) δ2.29 (s, 3H), 6.65 (d, 1H), 6.76 (s, 1H), 6.81 (d, 1H), 7.05 (m, 5H), 7.25–7.47 (comp m, 13H), 7.71 (m, 2H).

Step C: Preparation of 2-(1-triphehylmethyltetrazol-5-yl)-5-bromomethyl-2-phenyl-1,3-benzodioxole (compound 3c where X=O)

To a solution of the product of Step B (45 mg, 0.086 mmoL) in dry CCl$_4$ (2 mL) under N$_2$ was added NBS (14 mg, 0.91 equiv) and a catalytic amount of AlBN. After stirring at reflux for 2 h the mixture was cooled to rt, diluted with diethyl ether and filtered through a plug of cotton. The filtrate was concentrated in vacuo and the residue was purified by flash chromatography eluting with hexane/ethyl acetate (15:1) to afford 40.5 mg of the titled compound. Rf=0.18 (15:1 hexane/ethyl acetate).

Step D: Preparation of 2-(1'H-tetrazol-5'-yl)-5-[3"-(7"-methyl-2'-propylimidazopyridinyl)]-2-phenyl-1,3-benzodioxole (compound 3d where X=O)

To a solution of 7-methyl-2-propylimidazopyridine (24 mg, 0.137 mmoL), prepared according to the procedures described in EP 400,974 pub. date Dec. 5, 1990, in dry DMF (1 mL) under N$_2$ was added 60% NaH in oil (7 mg, 1.3 equiv). After stirring at rt for 30 min a solution of the product of Step C (40.5 mg, 0.067 mmoL) in DMF (0.5 mL) was added. After stirring at rt for 30 min the reaction was quenched with H$_2$O and the DMF was removed. The residue was purified by flash chromatography eluted with ethyl acetate/hexane (1.2:1) to afford 15.4 mg (33%) of the title compound protected as the trityl derivative. The trityl group was removed as follows: To a solution of the protected compound (15.4 mg, 0.022 mmoL) in CH$_3$OH (2 mL) was added 7 drops of acetic acid. After 3 h the mixture was concentrated and the residue was purified by flash chromatography eluting with CH$_2$Cl$_2$/CH$_3$OH/NH$_4$OH (100:20:1) to afford 8.8 mg of the titled compound.

1H NMR (300 MHz, CD$_3$OD) δ0.89 (t, 3H), 1.65 (m, 2H), 2.63 (s, 3H), 2.85 (t, 2H), 5.49 (s, 2H), 6.68 (d, 1H), 6.79 (s, 1H), 6.87 (d, 1H), 7.13 (d, 1H), 7.38 (m, 3H), 7.58 (m, 2H), 8.20 (d, 1H).

EXAMPLE 5

2-(4-methylphenyl)-5-[(7-methyl-2-propyl-3H-imidazo[4,5-B]pyridin-3-yl)methyl]-1,3-Benzodithiole-2-carboxylic acid (Scheme II-4, compound 4e, where X=S)

Step A: Preparation of Ethyl 5-methyl-2-(4-methylphenyl)-1,3-benzodithiole-2-carboxylate (scheme II-4, compound 4c where X=S)

To a solution of ethyl 4-methylbenzoylformate (2.72 g, 14.2 mmoL) in benzene (12 mL) was added PCl$_5$ (5.89 g, 2.0 equiv). The mixture was stirred at reflux for 4 h. The crude product, 4a was used in the next step. To a solution of 3,4-dithioltoluene (432 mg, 2.77 mmoL) in isopropanol (5 mL) was added K$_2$CO$_3$ (1.19 g, 5 equiv) and 4a (531 mg, 2.16 mmoL). The mixture was stirred at reflux for 24 h. The majority of the isopropanol was removed with a stream of N$_2$ and the residue was taken up in diethyl ether and washed with 1N NaOH, H$_2$O and brine. The organic was dried over anhydrous MgSO$_4$ and concentrated in vacuo. The product was purified by flash chromatography eluting with hexane/ethyl acetate (30:1) to afford 200 mg (28%) of the titled compound. Rf=0.36 (25:1 hexane/ethyl acetate).

1H NMR (250 MHz, CDCl$_3$) δ1.22 (t, 3H), 2.27 (s, 3H), 2.36 (s, 3H), 4.25 (q, 2H), 6.83 (d, 1H), 7.06 (s, 1H), 7.11 (d, 1H), 7.14 (d, 2H), 7.62 (d, 2H).

Step B: Preparation of Ethyl 5-bromomethyl-2-(4-methylphenyl)-1,3-benzodithiole-2-carboxylate (Scheme II-4, compound 4d where X=S)

To a solution of the product of Step A (200 mg 0.606 mmoL) in dry CCl4 (5 mL) was added a catalytic amount of AlBN and NBS (81 mg, 0.75 equiv). The reaction was stirred at reflux under N$_2$ for 4 h. The solution was allowed to cool to rt and the succinimide was removed by filtration through a plug of cotton. The filtrate was concentrated and the residue purified by flash chromatography eluting with hexane/ethyl acetate (30:1) to afford 124 mg (50%) of the titled compound. Rf=0.33 (25:1 hexane/ethyl acetate).

1H NMR (250 MHz, CDCl$_3$) δ1.22 (t, 3H), 2.36 (s, 3H), 4.25 (q, 2H), 4.39 (s, 2H), 7.05 (d, 1H), 7.16 (d, 2H), 7.25 (d, 2H), 7.61 (d, 2H).

Step C: Preparation of 2-(4methylphenyl)-5-[(7-methyl-2-propyl-3H-imidazo[4,5-B]pyridin-3-yl)methyl]-1,3-Benzodithiole-2-carboxylic acid (Scheme II-4, compound 4e where X=S)

To a solution of 7-methyl-2-propylimidazopyridine (36 mg, 0.21 mmoL), prepared according to the procedures described in EP 400,974 pub. date Dec. 5, 1990, in dry DMF (1 mL) under N$_2$ was added 60% NaH in oil (12 mg, 1.5 equiv). After stirring for 20 min a solution of the product of Step B (41 mg, 0.10 mmoL) in DMF (0.5 mL) was added. After 15 min the mixture was quenched with sat'd NH4Cl soln and the DMF was removed under high vacuum. The residue was taken up in ethyl acetate and filtered. The filtrate was concentrated in vacuo and the product was purified by flash chromatography eluting with ethyl acetate/hexane (1:1) to afford 9.1 mg (18%) of the coupled product (the ethyl ester of the titled compound). To a solution of the coupled product in dry CH3OH (2 mL) was added 1N NaOH (15 drops). After 2 h the reaction appeared, by TLC anlaysis, to have gone to completion. The mixture was quenched with acetic acid and concentrated in vacuo. The residue as purified by flash chromatography eluting with CH2Cl2/CH3OH/NH4OH (100:15:1) to afford 10.1 mg (98%) of the titled compound as an acetic acid salt. Rf=0.38 (100:15:1 CH2Cl2/CH3OH/NH4OH).

1H NMR (250 MHz, CD3OD) δ0.87 (t, 3H), 1.61 (m, 2H), 1.92 (s, 3H), 2.23 (s, 3H), 2.62 (s, 3H), 2.79 (t, 2H), 5.41 (s, 2H), 6.71 (d, 1H), 6.95 (s, 1H), 7.03 (d, 2H), 7.08 (d, 1H), 7.12 (d, 1H), 7.68 (d, 2H), 8.16 (d, 1H).

EXAMPLE 6

5-[(2-ethyl-5,7-dimethyl-3H-imidazo[4,5-B]pyridin-3-yl)methyl]-2-(4-methylphenyl]-1,3-Benzodioxole-2-carboxylic acid (Scheme II-5, compound 5b where X=O)

The titled compound was prepared by alkylating 2-ethyl-5,7-dimethylimidazopyridine, prepared according to the procedures described in EP 400,974 pub. date Dec. 5, 1990, with the product of Example 5, Step B followed by the same procedures used to prepare the product of example 6.

1H NMR (300 MHz, CD3OD) δ1.39 (t, 3H), 2.37 (s, 3H), 2.62 (s, 3H), 5.48 (s, 2H), 6.67 (d, 1H), 6.75 (s, 1H), 6.82 (d, 1H), 7.05 (s, 1H), 7.20 (d, 2H), 7.59 (d, 2H).

Using the procedures described above the following compounds can be prepared:

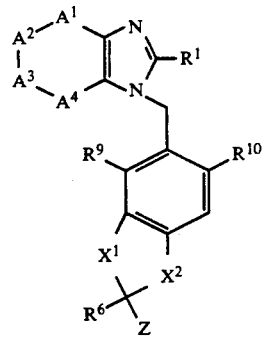

| $A^1-A^2-A^3-A^4-$ | $R^1$ | $R^9$ | $R^{10}$ | $X^1, X^2$ | $R^6$ | Z |
|---|---|---|---|---|---|---|
| —CH=CH—CH=CH— | n-butyl | H | H | O, O | phenyl | CO2H |
| —CH=CH—CH=CH— | n-butyl | H | H | O, O | p-tolyl | CO2H |
| —CH=CH—CH=CH— | n-propyl | H | H | S, S | phenyl | tetrazol-5-yl |
| —C(CH3)=CH—CH=N— | propyl | H | H | O, O | phenyl | CO2H |
| —C(CH3)=CH—CH=N— | propyl | H | H | O, O | p-tolyl | CO2H |
| —C(CH3)=CH—CH=N— | propyl | H | H | O, O | phenyl | tetrazol-5-yl |
| —C(CH3)=CH—CH=N— | propyl | H | H | O, O | p-tolyl | tetrazol-5-yl |
| —C(CH3)=CH—CH=N— | ethyl | H | H | S, S | phenyl | CO2H |
| —C(CH3)=CH—CH=N— | ethyl | H | H | O, S | p-tolyl | tetrazol-5-yl |
| —C(CH3)=CH—C(CH3)=N— | ethyl | H | H | O, S | phenyl | CO2H |
| —C(CH3)=CH—C(CH3)=N— | ethyl | H | H | S, O | p-tolyl | CO2H |
| —C(CH3)=CH—C(CH3)=N— | ethyl | propyl | H | O, O | phenyl | tetrazol-5-yl |
| —C(CH3)=N—CH=N— | ethyl | H | H | O, O | phenyl | CO2H |
| —C(CH3)=N—CH=N— | propyl | propyl | H | O, O | p-tolyl | CO2H |
| —C(CH3)=N—CH=N— | butyl | propyl | propyl | O, O | phenyl | tetrazol-5-yl |
| —C(CH3)=N—C(CH3)=N— | ethyl | H | H | O, O | phenyl | CO2H |
| —C(CH3)=N—C(CH3)=N— | propyl | H | H | O, O | p-tolyl | CO2H |
| —CH=CH—CH=N— | ethyl | H | H | O, O | p-tolyl | CO2H |
| —CH=CH—CH=N— | propyl | H | H | S, S | phenyl | CO2H |

What is claimed is:
1. A compound of structural formula:

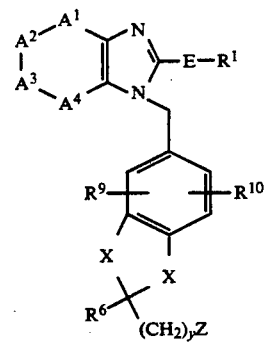

or a pharmaceutically acceptable salt thereof wherein:
$R^1$ is:
(a) (C1-C6)-alkyl, (C2-C6)-alkenyl or (C2-C6)-alkynyl each of which can be unsubstituted or substituted with a substituent selected from the group consisting of:
  i) aryl as defined below in $R^1$(b),
  ii) (C3-C7)-cycloalkyl,
  iii) Cl, Br, I, F,
  iv) OH,
  v) NH2,
  vi) NH(C1-C4)-alkyl, vii) N[((C$_1$–C$_4$)-alkyl)]$_2$,
viii) NHSO$_2$R$^2$,
ix) CF$_3$,
x) COOR$^2$, or
xi) SO$_2$NHR$^{2a}$;
(b) aryl, wherein aryl is defined as phenyl or naphthyl, unsubstituted or substituted with 1 or 2 substituents selected from the group consisting of:
  i) Cl, Br, I, F,
  ii) (C$_1$–C$_4$)-alkyl,
  iii) (C$_1$–C$_4$)-alkoxy,
  iv) NO$_2$
  v) CF$_3$
  vi) SO$_2$NR$^{2a}$R$^{2a}$,
  vii) (C$_1$–C$_4$)-alkylthio,
  viii) hydroxy,
  ix) amino,
  x) (C$_3$–C$_7$)-cycloalkyl,
  xi) (C$_3$–C$_{10}$)-alkenyl; and
(c) heteroaryl, wherein heteroaryl is defined as a 5- or 6-membered heteroaromatic moiety, which can contain one or two members selected from the group consisting of N, O, S and wherein the heteroaryl is optionally mono- or disubstituted with substituents selected from the group consisting of:
  i) Cl, Br, I, F,
  ii) OH,
  iii) SH,
  iv) NO$_2$,
  v) (C$_1$–C$_4$)-alkyl,
  vi) (C$_2$–C$_4$)-alkenyl,
  vii) (C$_2$–C$_4$)-alkynyl,
  viii) C$_1$–C$_4$-alkoxy, or
  ix) CF$_3$,
(d) (C$_1$–C$_4$)-perfluoroalkyl,
(e) (C$_3$–C$_8$)-cycloalkyl, or
(f) (C$_1$–C$_4$)-alkyl-(C$_3$–C$_8$)-cycloalkyl;
—A$^1$—A$^2$—A$^3$—A$^4$— is:
  (a) —C(R$^4$)=C(R$^4$)—C(R$^4$)=N—,
  (b) —N=C(R$^4$)—C(R$^4$)=C(R$^4$)—,
  (c) —C(R$^4$)=N—C(R$^4$)=C(R$^4$)—, or
  (d) —C(R$^4$)=C(R$^4$)—N=C(R$^4$)—;
E is:
  (a) a single bond,
  (b) —S(O)$_n$(CH$_2$)$_s$—, or
  (c) —O—;
n is 0 to 2;
s is 0 to 5;
y is 0 or 1;
X groups are independently:
  —O— or —S—;
R$^2$ is:
  (a) H, or
  (b) (C$_1$–C$_6$)-alkyl;
R$^{2a}$ is:
  (a) R$^2$,
  (b) CH$_2$-aryl, or
  (c) aryl;
R$^4$ groups are independently:
  (a), H,
  (b) (C$_1$–C$_6$)-alkyl, (C$_2$–C$_6$)-alkenyl or (C$_1$–C$_6$)-alkynyl, each of which is unsubstituted or substituted with a substituent selected from the group consisting of: OH, (C$_1$–C$_4$)-alkoxy, CO$_2$R$^2$, OCOR$^2$, CONHR$^2$, CON(R$^2$)$_2$, N(R$^2$)C(=O)R$^2$, NH$_2$, NH[(C$_1$–C$_4$)-alkyl], N[(C$_1$–C$_4$)-alkyl]$_2$,
  (c) —C(=O)—aryl,
  (d) (C$_3$–C$_7$)-cycloalkyl,
  (e) Cl, Br, I, F,
  (f) —OH,
  (g) —OR$^{21}$,
  (h) —CF$_3$,
  (i) —SH,
  (j) —S(O)$_n$—(C$_1$–C$_4$)-alkyl,
  (k) —CO$_2$R$^{2a}$,
  (l) —SO$_3$H,
  (m) —NR$^2$R$^{21}$,
  (n) —NR$^2$C(O)R$^{21}$,
  (o) —NR$^2$COOR$^{21}$,
  (p) —SO$_2$NR$^2$R$^{2a}$,
  (q) —NO$_2$,
  (r) —NHSO$_2$—(C$_1$–C$_4$)-alkyl,
  (s) —C(O)NHSO$_2$R$^{14}$,
  (t) aryl,
  (u) heteroaryl, or
  (v) morpholin-4-yl;
R$^6$ is:
  (a) H,
  (b) (C$_1$–C$_4$)-alkyl,
  (c) aryl, wherein aryl is phenyl or naphthyl, substituted or unsubstituted with one or two substituents selected from the group consisting of: (C$_1$–C$_4$)-alkyl, (C$_1$–C$_4$)-alkoxyl, (C$_1$–C$_4$)-alkyl-S(O)$_n$—, —CO$_2$R$^2$, Cl, Br, I, F, CONR$^2$R$^{2a}$, NHCO(C$_1$–C$_4$)-alkyl, NHCONR$^2$R$^{2a}$, O-phenyl, or S-phenyl; or
  (d) aryl-(C$_1$–C$_2$)-alkyl;
R$^9$ and R$^{10}$ are each independently:
  (a) H,
  (b) Cl, Br, I, F,
  (c) NO$_2$,
  (d) (C$_1$–C$_8$)-alkyl,
  (e) (C$_2$–C$_4$)-alkenyl,
  (f) (C$_2$–C$_4$)-alkynyl,
  (g) (C$_1$–C$_4$)-alkoxy,
  (h) (C$_1$–C$_4$)-alkylthio,
  (i) (C$_1$–C$_4$)-alkylsulfinyl, or
  (j) (C$_1$–C$_4$)-alkylsulfonyl;
when y=1, Z is:
  (a) —CO$_2$R$^{2a}$,
  (b) —tetrazol-5-yl,
  (c) —PO(OH)$_2$,
  (d) —CONH(tetrazol-5-yl),
  (e) —CH$_2$CO$_2$R$^{2a}$,
  (f) —CONHSO$_2$R$^{14}$,
when y=0, then Z can be:
  (g) —CO$_2$R$^{2a}$,
  (h) —tetrazol-5-yl,
  (i) —CONH(tetrazol-5-yl),
  (j) —NHSO$_2$CF$_3$, or
  (k) —CONHSO$_2$R$^{14}$;
R$^{14}$ is:
  (a) aryl,
  (b) heteroaryl,
  (c) (C$_3$–C$_7$)-cycloalkyl, or
  (d) (C$_1$–C$_4$)-alkyl unsubstituted or substituted with a substituent selected from the group consisting of: aryl, heteroaryl, —OH, —SH, (C$_1$–C$_4$)-alkyl, —O(C$_1$–C$_4$) alkyl, —S(C$_1$–C$_4$)-alkyl, —CF$_3$, Cl, Br, F, I, —NO$_2$, —CO$_2$H, CO$_2$—(C$_1$–C$_4$)-alkyl, NH$_2$, NH[(C$_1$–C$_4$)alkyl], N[(C$_1$–C$_4$)-alkyl]$_2$, —PO$_3$H, PO(OH)(O—(C$_1$–C$_4$)-alkyl); and
R$^{21}$ is:
  (a) H, or (b) $C_1$–$C_4$)-alkyl, unsubstituted or substituted with a substituent selected from the group consisting of: $NH_2$, $NH[(C_1$–$C_4)$-alkyl], $N[(C_1$–$C_4)$-alkyl]$_2$, $CO_2H$, $CO_2(C_1$–$C_4)$-alkyl, OH, $SO_3H$, or $SO_2NH_2$.

2. The compound of claim 1, wherein $R^9$ and $R^{10}$ are H or $(C_1$–$C_3)$-alkyl; X groups are independently O or S; $R^6$ is phenyl, unsubstituted or substituted with a substituent selected from the group consisting of: $(C_1$–$C_4)$-alkyl, $(C_1$–$C_4)$-alkoxyl, $(C_1$–$C_4)$-alkyl-S(O)$_n$—, —$CO_2R^2$, Cl, Br, I, F, $CONR^2R^{2a}$, $NHCO(C_1$–$C_4)$-alkyl, $NHCONR^2R^{2a}$, O-phenyl, or S-phenyl; y is 0; and Z is $CO_2H$ or tetrazol-5-yl.

3. The compound of claim 2, wherein $R^9$ and $R^{10}$ are H; X groups are both O or S; and $R^6$ is phenyl.

4. A compound of structural formula

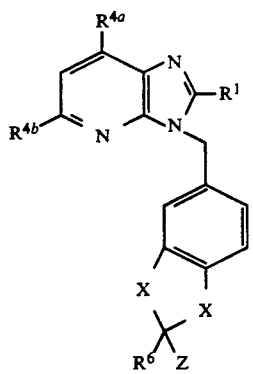

wherein the substituents are as defined below:

| X, X | $R^1$ | $R^6$ | Z | $R^{4a}$ | $R^{4b}$ |
|------|-------|-------|---|----------|----------|
| O, O | propyl | phenyl | $CO_2H$ | $CH_3$ | H |
| S, S | propyl | phenyl | $CO_2H$ | $CH_3$ | H |
| O, O | propyl | phenyl | tetrazol-5-yl | $CH_3$ | H |
| S, S | propyl | p-tolyl | $CO_2H$ | $CH_3$ | H |
| O, O | ethyl | p-tolyl | $CO_2H$ | $CH_3$ | $CH_3$ |
| O, O | propyl | p-tolyl | $CO_2H$ | $CH_3$ | H |
| O, O | propyl | p-tolyl | tetrazol-5-yl | $CH_3$ | H |
| S, S | ethyl | p-tolyl | $CO_2H$ | $CH_3$ | H |
| O, S | ethyl | p-tolyl | tetrazol-5-yl | $CH_3$ | H |
| O, S | ethyl | phenyl | $CO_2H$ | $CH_3$ | $CH_3$ |
| S, O | ethyl | p-tolyl | $CO_2H$ | $CH_3$ | $CH_3$ |
| O, O | ethyl | p-tolyl | $CO_2H$ | H | H |
| S, S | propyl | phenyl | $CO_2H$ | H | H. |

5. A pharmaceutical composition useful in the treatment of hypertension which comprises a pharmaceutically acceptable carrier and a therapeutically effective amount of a compound of claim 1.

6. A method of treating hypertension which comprises administering to a patient in need of such treatment a therapeutically effective amount of a compound of claim 1.

7. An ophthalmological formulation for the treatment of ocular hypertension comprising an ophthalmologically acceptable carrier and an effective ocular antihypertensive amount of a compound of claim 1.

8. A method of treating ocular hypertension comprising topical ocular administration to a patient in need of such treatment of an effective ocular antihypertensive amount of a compound of claim 1.

9. A method of treating cognitive dysfunction, anxiety, or depression comprising administering to a patient in need of such treatment, a therapeutically effective amount of a compound of claim 1.

* * * * *